United States Patent [19]

O'Sullivan

[11] Patent Number: 5,122,618
[45] Date of Patent: Jun. 16, 1992

[54] INSECTICIDES AND PARASITICIDES

[75] Inventor: Anthony C. O'Sullivan, Basel, Switzerland

[73] Assignee: Ciba-Geigy Corporation, Ardsley, N.Y.

[21] Appl. No.: 600,037

[22] Filed: Oct. 17, 1990

Related U.S. Application Data

[62] Division of Ser. No. 472,680, Jan. 30, 1990, abandoned, which is a division of Ser. No. 317,387, Mar. 1, 1989, Pat. No. 4,918,097.

[30] Foreign Application Priority Data

Mar. 11, 1988 [CH] Switzerland ............................ 934/88

[51] Int. Cl.$^5$ .......................................... C07D 315/00
[52] U.S. Cl. .................................................. 549/264
[58] Field of Search .......................................... 549/264

[56] References Cited

U.S. PATENT DOCUMENTS

| Re. 32,034 | 11/1985 | Chabala et al. | 549/264 |
|---|---|---|---|
| 3,950,360 | 4/1976 | Aoki et al. | 549/264 |
| 4,173,571 | 11/1979 | Chabala et al. | 549/264 |
| 4,346,171 | 8/1982 | Takiguchi et al. | 549/264 |
| 4,696,922 | 9/1987 | Sturm et al. | 549/264 |
| 4,696,945 | 9/1987 | Frei et al. | 549/264 |
| 4,918,097 | 4/1990 | O'Sullivan | 549/264 |
| 4,945,105 | 7/1990 | Sato et al. | 549/264 |

FOREIGN PATENT DOCUMENTS

| 0008184 | 2/1980 | European Pat. Off. |
|---|---|---|
| 0180539 | 9/1984 | European Pat. Off. |
| 0215654 | 3/1987 | European Pat. Off. |
| 0237340 | 9/1987 | European Pat. Off. |
| 0241145 | 10/1987 | European Pat. Off. |
| 0262384 | 4/1988 | European Pat. Off. |
| 0266131 | 5/1988 | European Pat. Off. |
| 0282456 | 9/1988 | European Pat. Off. |
| 0284255 | 9/1988 | European Pat. Off. |
| 2717040 | 11/1977 | Fed. Rep. of Germany |
| 3631387 | 3/1987 | Fed. Rep. of Germany |

OTHER PUBLICATIONS

Sheverdina et al.—The Preparation of Aromatic, Heterocyclic, and Mixed Aromatic-Aliphatic . . . , pp. 299–301.
Hajime Matsushita et al., J. Chem. Soc., Chem. Commun., pp. 160–161 (1982).
The Molecular Basis of Antibiotic Action—John Wiley & Sons, 1981, p. 468.
Acc. Chem. Res., 1982, 15, 340–348.
J. Chem. Soc., Chem. Comm., 1982, 160–161.
Chemistry Lett., 1982, 141–142.
Tetrahedron Lett., 21, 351–354.

Primary Examiner—C. Warren Ivy
Assistant Examiner—Amelia A. Owens
Attorney, Agent, or Firm—Edward McC. Roberts

[57] ABSTRACT

The present invention relates to novel derivatives of formula I that can be derived from milbemycins, to their preparation and their use for controlling pests, and also to pesticides that contain at least one of these compounds as active ingredient.

The novel compounds have the general formula I

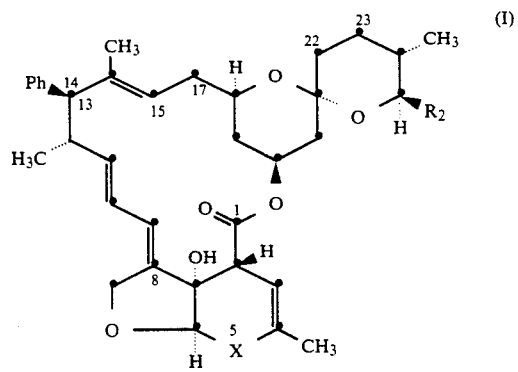

in which
X is one of the groups —CH(OR$_1$)—, —C(O)— or —C(=N—OR)—;
R$_1$ is hydrogen or an OH-protecting group;
R is hydrogen, an OH-protecting group, or an alkyl or cycloalkyl group;
R$_2$ is methyl, ethyl, isopropyl or sec.-butyl; and
Ph is a phenyl ring that is substituted by R$_a$, R$_b$, R$_c$ and R$_d$, wherein each of R$_a$, R$_b$, R$_c$ and R$_d$, independently of the others, is hydrogen, C$_1$–C$_{10}$alkyl, C$_2$–C$_{10}$alkoxyalkyl, C$_2$–C$_{10}$alkenyl, C$_1$–C$_{10}$alkoxy, C$_2$–C$_{10}$alkoxyalkoxy, or a phenyl or phenoxy radical that is unsubstituted or is substituted by at least one substituent from the group C$_1$–C$_3$alkyl and C$_1$–C$_3$alkoxy.

3 Claims, No Drawings

INSECTICIDES AND PARASITICIDES

This is a divisional of application Ser. No. 472,680 filed on Jan. 30, 1990, now abandoned which is a divisional of Ser. No. 317,387 filed Mar. 1, 1989, now U.S. Pat. No. 4,918,097.

The present invention relates to novel derivatives of formula I that can be derived from milbemycins, to their preparation and their use for controlling pests, and also to pesticides that contain at least one of these compounds as active ingredient.

The novel compounds have the general formula I

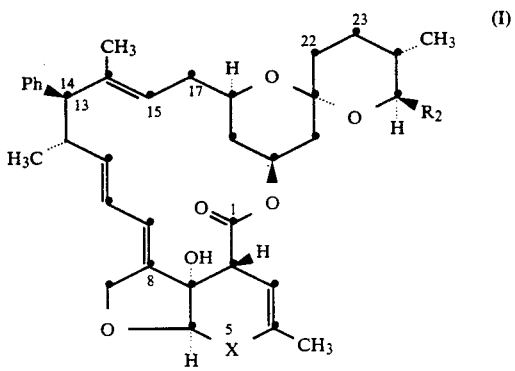

in which

X is one of the groups —CH(OR$_1$)—, —C(O)— or —C(=N—OR)—;

R$_1$ is hydrogen or an OH-protecting group;

R is hydrogen, an OH-protecting group, or an alkyl or cycloalkyl group;

R$_2$ is methyl, ethyl, isopropyl or sec.-butyl; and

Ph is a phenyl ring that is substituted by R$_a$, R$_b$, R$_c$ and R$_d$, wherein each of R$_a$, R$_b$, R$_c$ and R$_d$, independently of the others, is hydrogen, C$_1$-C$_{10}$alkyl, C$_2$-C$_{10}$alkoxyalkyl, C$_2$-C$_{10}$alkenyl, C$_1$-C$_{10}$alkoxy, C$_2$-C$_{10}$alkoxyalkoxy, or a phenyl or phenoxy radical that is unsubstituted or is substituted by at least one substituent from the group C$_1$-C$_3$alkyl and C$_1$-C$_3$alkoxy.

The term "alkyl" as an independent substituent or as a component of a substituent is used to mean, depending on the number of carbon atoms indicated, methyl, ethyl, propyl, butyl, pentyl, hexyl, heptyl, octyl, nonyl and decyl, and any suitable isomers thereof, such as, for example, isopropyl, isobutyl, tert.-butyl and isopentyl. R as alkyl is preferably alkyl having from 1 to 8, especially from 1 to 4, carbon atoms.

Cycloalkyl is preferably C$_3$-C$_6$cycloalkyl, that is to say cyclopropyl, cyclobutyl, cyclopentyl and cyclohexyl.

C$_2$-C$_{10}$alkoxyalkyl is an alkyl radical having a carbon structure that consists of up to 10 carbon atoms and that is interrupted at one position by an oxygen atom. Preferred alkoxyalkyl groups are those having from 1 to 6 carbon atoms, such as, for example, —CH$_2$—O—CH$_3$, —CH$_2$—O—C$_2$H$_5$, —CH$_2$CH$_2$—O—C$_2$H$_5$, —CH$_2$CH$_2$—O—CH$_3$, —CH(CH$_3$)—O—CH$_3$, —CH$_2$—O—C(CH$_3$)$_3$, —C(CH$_3$)$_2$—O—CH$_3$ or —CH$_2$CH$_2$CH$_2$—O—$n$C$_3$H$_7$.

C$_2$-C$_{10}$alkenyl is a straight-chain or branched acyclic, aliphatic radical having a double bond. Especially worthy of mention is C$_2$-C$_4$alkenyl, for example vinyl and allyl.

Of the C$_1$-C$_{10}$alkoxy groups, those having from 1 to 6 carbon atoms are preferred. Examples are propoxy, ethoxy and, especially, methoxy.

C$_2$-C$_{10}$alkoxyalkoxy is an alkoxy radical having a carbon structure that consists of up to 10 carbon atoms and that is interrupted at one position by an oxygen atom. Preferred alkoxyalkoxy groups are those having from 2 to 6 carbon atoms, such as, for example, —O—CH$_2$CH$_2$—O—C$_2$H$_5$, —O—CH$_2$CH$_2$—O—CH$_3$, O—CH$_2$CH$_2$CH$_2$—O—$n$C$_3$H$_7$, —O—CH$_2$—C(CH$_3$)$_2$—O—CH$_3$, —O—CH$_2$—O—CH$_3$ or —O—CH$_2$CH$_2$CH$_2$CH$_2$—O—CH$_3$, and also —O—CH$_2$CH$_2$—O—CH$_2$—C(CH$_3$)$_3$.

Preferred substituted phenyl and phenoxy radicals R$_a$, R$_b$, R$_c$ and R$_d$ are those which are substituted by from 1 to 3 substituents from the group C$_1$-C$_3$alkyl and C$_1$-C$_3$alkoxy, and especially those in which the total number of carbon atoms of all the substituents of one ring when taken together does not exceed the number 5. Preferred substituents of the phenyl and phenoxy radicals are methyl and methoxy.

Ph is especially phenyl, a phenyl radical substituted by from one to three methyl groups, a phenyl radical substituted by from one to three methoxy groups, or a phenyl radical substituted by one phenyl or one phenoxy group.

Suitable structural elements symbolised by "Ph" are those which can be derived from compounds that are obtainable by customary chemical methods.

Throughout this specification, OH-protecting groups for the substituents R and R$_1$ are to be understood as being the protective functions that are customary in organic chemistry. These are especially acyl and silyl groups. Suitable acyl groups are, for example, the radicals R$_4$—C(O)—, wherein R$_4$ is C$_1$-C$_{10}$alkyl, C$_1$-C$_{10}$haloalkyl, or a group from the series phenyl and benzyl that is unsubstituted or is substituted by one or more substituents selected from the group consisting of halogen, C$_1$-C$_3$alkyl, C$_1$-C$_3$haloalkyl, C$_1$-C$_3$alkoxy, C$_1$-C$_3$haloalkoxy, cyano and nitro, and is preferably C$_1$-C$_6$alkyl, C$_1$-C$_6$haloalkyl, or phenyl that is unsubstituted or is substituted by halogen, C$_1$-C$_3$alkyl, CF$_3$ or by nitro. A suitable silyl group for R$_1$ and R is the radical —Si(R$_5$)(R$_6$)(R$_7$), wherein R$_5$, R$_6$ and R$_7$, preferably independently of one another, are C$_1$-C$_4$alkyl, benzyl or phenyl and form, for example, together with the silicon atom, one of the groups trimethylsilyl, tris(tert.-butyl)silyl, diphenyl-tert.-butylsilyl, bis(isopropyl)methylsilyl, triphenylsilyl etc. and, especially, tert.-butyldimethyl-silyl. The 5—OH group may also be etherified in the form of benzyl ether or methoxyethoxy methyl ether.

Compounds of formula I wherein X is the group —CH(or$_1$)— or —C(=N—OR)—, and R$_1$ and R are each a protecting group can be converted into the highly active free 5-hydroxy derivatives (R$_1$=H) or the 5-oxime derivatives (R=H) by simple removal of the protecting function, for example by hydrolysis, and thus have also the character of intermediates. The biological value of these compounds is not, however, reduced at all or to any significant extent by the protecting group. The removal of the protecting group by hydrolysis can be effected with a dilute acid, for example with 1% p-toluenesulfonic acid in methanol or with an aqueous HF solution in acetonitrile at from −20° C. to 50° C., preferably at from 0° C. to 30° C., or alternatively with pyridinium fluoride in pyridine.

The above-mentioned acyl and silyl groups serve as protecting groups not only for hydroxy groups present in the substituent X but also for all other hydroxy groups present in the compounds of the invention or in precursors of those compounds.

Compounds of formula I wherein X is —CH(OR$_1$)— and R$_1$ is hydrogen are preferred. Acyl and silyl groups as R and R$_1$ are generally to be regarded as protecting groups.

Throughout this specification, compounds in which R$_2$ is sec.-butyl are also to be classified as milbemycin derivatives although, according to conventional classification, they are derived from avermectin derivatives. Avermectin aglycons (having an OH group in the 13 α-position) can, however, be converted into milbemycin homologues in accordance with U.S. Pat. No. 4,173,571.

In naturally occurring milbemycins (X=—CH(OR$_1$)—, R$_1$=H; R$_2$=CH$_3$, C$_2$H$_5$ or isoC$_3$H$_7$) the 13-position is always occupied only by hydrogen:

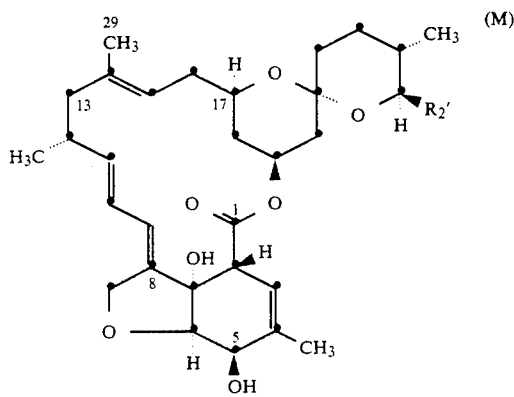

(M)

R$_{2'}$ = $_{CH_3}$milbemycin A$_3$ (U.S. Pat. No. 3,950,360)
R$_{2'}$ = $_{C_2H_5}$milbemycin A$_4$ (U.S. Pat. No. 3,950,360)
R$_{2'}$ = $_{isoC_3H_7}$milbemycin D (U.S. Pat. No. 4,346,171)
R$_{2'}$ = sec.-C$_4$H$_9$ 13-deoxy-22,23-dihydro-C-076-Bla-aglycon (U.S. Pat. No. 4,173,571, GB 1,573,955 and DE-OS 2 717 040)

In avermectins on the other hand, an α-L-oleandrosyl-α-L -oleandrose radical, which is linked via oxygen in α-configuration to the macrolide molecule, is present in the 13-position. Avermectins also differ structurally from milbemycins by a 23—OH group or Δ$^{22,23}$-double bond and, as a rule, by a substituent R$_2$=sec.—C$_4$H$_9$. Hydrolysis of the sugar residue of avermectins readily produces the corresponding avermectin aglycons that contain an allylic 13α-hydroxy group. As stated above, avermectin aglycons can be converted into milbemycin homologues. In the milbemycin derivatives of this application, the Δ$^{22,23}$-double bond is always in hydrogenated form.

Owing to their pronounced parasiticidal and insecticidal activity, the following subgroups of compounds of formula I according to the present invention are especially preferred:

Group Ia: Compounds of formula I wherein X is —CH(OR$_1$) — and R$_1$ is hydrogen or a protecting group, R$_2$ is methyl, ethyl, isopropyl or sec.-butyl; and Ph is a phenyl ring that is substituted by R$_a$, R$_b$, R$_c$ and R$_d$, wherein each of R$_a$, R$_b$, R$_c$ and R$_d$, independently of the others, is hydrogen, C$_1$-C$_{10}$alkyl, C$_2$-C$_{10}$alkoxyalkyl, C$_2$-C$_{10}$alkenyl, C$_1$-C$_{10}$alkoxy, C$_2$-C$_{10}$alkoxyalkoxy, or a phenyl or phenoxy radical that is unsubstituted or is substituted by at least one substituent from the group C$_1$-C$_3$alkyl and C$_1$-C$_3$alkoxy.

Group Ib: Compounds of formula I wherein X is —CH(OR$_1$) — and R$_1$ is hydrogen, R$_2$ is methyl, ethyl, isopropyl or sec.-butyl; and Ph is a phenyl ring that is substituted by R$_a$, R$_b$, R$_c$ and R$_d$, wherein each of R$_a$, R$_b$, R$_c$ and R$_d$, independently of the others, is hydrogen, C$_1$-C$_{10}$alkyl, C$_2$-C$_{10}$alkoxyalkyl, C$_2$-C$_{10}$alkenyl, C$_1$-C$_{10}$alkoxy, C$_2$-C$_{10}$alkoxyalkoxy, or a phenyl or phenoxy radical that is unsubstituted or is substituted by at least one substituent from the group C$_1$-C$_3$alkyl and C$_1$-C$_3$alkoxy.

Group Ic: Compounds of formula I wherein X is —CH(OR$_1$)— and R$_1$ is hydrogen, R$_2$ is methyl or ethyl; and Ph is a phenyl ring that is substituted by R$_a$, R$_b$, R$_c$ and R$_d$, wherein each of R$_a$, R$_b$, R$_c$ and R$_d$, independently of the others, is hydrogen, C$_1$-C$_{10}$alkyl, C$_2$-C$_{10}$alkoxyalkyl, C$_2$-C$_{10}$alkenyl, C$_1$-C$_{10}$alkoxy, C$_2$-C$_{10}$alkoxyalkoxy, or a phenyl or phenoxy radical that is unsubstituted or is substituted by at least one substituent from the group C$_1$-C$_3$alkyl and C$_1$-C$_3$alkoxy.

Group Id: Compounds of formula I wherein X is —CH(OR$_1$)— and R$_1$ is hydrogen, R$_2$ is methyl or ethyl; and Ph is a phenyl ring that is substituted by R$_a$, R$_b$, R$_c$ and R$_d$, wherein each of R$_a$, R$_b$, R$_c$ and R$_d$, independently of the others, is hydrogen, C$_1$-C$_{10}$alkyl, C$_2$-C$_{10}$alkoxyalkyl, C$_2$-C$_{10}$alkenyl, C$_1$-C$_{10}$alkoxy or C$_2$-C$_{10}$alkoxyalkoxy.

Group Ie: Compounds of formula I wherein X is —CH(OR$_1$)— and R$_1$ is hydrogen, R$_2$ is methyl or ethyl; and Ph is a phenyl ring that is substituted by R$_a$, R$_b$, R$_c$ and R$_d$, wherein each of R$_a$, R$_b$, R$_c$ and R$_d$, independently of the others, is hydrogen, or a phenyl or phenoxy radical that is unsubstituted or is substituted by at least one substituent from the group C$_1$-C$_3$alkyl and C$_1$-C$_3$alkoxy.

Group If: Compounds of formula I wherein X is —CH(OR$_1$)— and R$_1$ is hydrogen, R$_2$ is methyl or ethyl; and Ph is a phenyl ring that is substituted by R$_3$, R$_b$, R$_c$ and R$_d$, wherein each of R$_a$, R$_b$, R$_c$ and R$_d$, independently of the others, is hydrogen, C$_1$-C$_3$alkyl or C$_1$-C$_3$alkoxy, with the proviso that not more than two of the substituents R$_a$, R$_b$, R$_c$ and R$_d$ have a meaning other than hydrogen.

Group Ig: Compounds of formula I wherein X is —CH(OR$_1$)— and R$_1$ is hydrogen, R$_2$ is methyl or ethyl; and Ph is a phenyl ring that is substituted by R$_a$, R$_b$, R$_c$ and R$_d$, wherein each of R$_a$, R$_b$, R$_c$ and R$_d$, independently of the others, is hydrogen, phenyl or phenoxy, with the proviso that not more than two of the substituents R$_a$, R$_b$, R$_c$ and R$_d$ have a meaning other than hydrogen.

Group Ih: Compounds of formula I wherein X is —CH(OR$_1$)— and R$_1$ is hydrogen, R$_2$ is methyl or, especially, ethyl; and Ph is phenyl that is unsubstituted or monosubstituted by methyl, methoxy, phenyl or phenoxy, or disubstituted by methyl or methoxy, or trisubstituted by methyl.

Group Ii: Compounds of formula I wherein X is —CH(OR$_1$)— and R$_1$ is hydrogen, R$_2$ is methyl or, especially, ethyl; and Ph is phenyl that is unsubstituted or monosubstituted by methyl, methoxy, phenyl or phenoxy, or disubstituted by methoxy.

Preferred individual compounds (X=—CH(OR$_1$)—, R$_1$=H) are:

13β-phenyl-milbemycin $A_4$,

13β-(2-methoxyphenyl)-milbemycin $A_4$,

13β-(3-methoxyphenyl)-milbemycin $A_4$,

13β-(4-methoxyphenyl)-milbemycin $A_4$,

13β-(2-methylphenyl)-milbemycin $A_4$,

13β-(4-biphenylyl)-milbemycin $A_4$,

13β-(4-phenoxyphenyl)-milbemycin $A_4$ and

13β-(3,4-dimethoxyphenyl)-milbemycin $A_4$.

The following compounds exhibit pronounced activity:

13β-phenyl-milbemycin $A_3$,

13β-(2-methylphenyl)-milbemycin $A_4$ and

13β-(4-methylphenyl)-milbemycin $A_4$.

The present invention relates not only to the compounds of formula I but also to novel processes for their preparation. It has been found that, surprisingly, the substituent "Ph" can be bonded in a deliberate manner stereospecifically in the β-configuration to the 13—C atom of the macrolide molecule by reacting the corresponding 13β-halogen compound or the corresponding 15-halogen-$\Delta^{13,14}$ derivative with an aryl metal compound, in which the aryl moiety corresponds to the substituent "Ph", in the presence of a catalytic amount of a transition metal salt. The reaction of compounds of the type

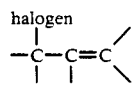

with aryl metal compounds, catalysed by a transition metal salt, is known from the literature (Acc. Chem. Res. 1982, 15, 340–348), and, as a rule, this reaction takes place with inversion. This means that, for example, when reacting a corresponding 13β-halogen-milbemycin derivative with an aryl metal compound, catalysed by a transition metal salt, the formation of a 13α-arylmilbemycin derivative is to be expected. Surprisingly, however, only 13β-arylmilbemycin derivatives are obtained.

Accordingly, the invention further relates to a process for the preparation of compounds of formula I, which process comprises reacting a compound of formula II

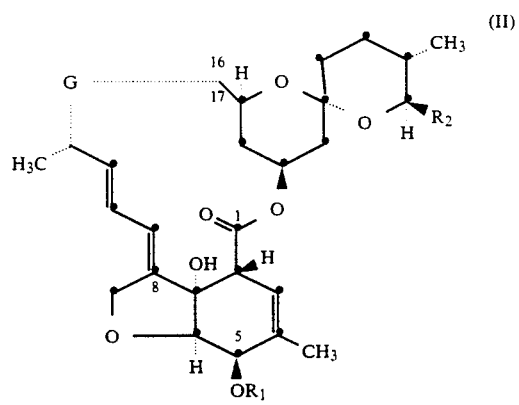

wherein G is one of the groups a or b

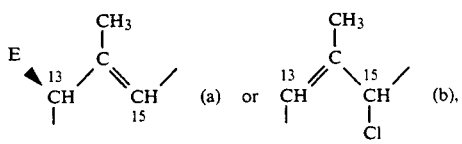

[= 13β-halogen-$\Delta^{14,15}$]    [= 15-chloro-$\Delta^{13,14}$]

$R_1$ is hydrogen or an OH-protecting group, $R_2$ is as defined for formula I, and E is chlorine, bromine or iodine, with a diaryl zinc compound of formula III $$Ph—Zn—Ph \qquad (III),$$

wherein Ph is as defined for formula I, in the presence of a transition metal salt, and, if desired, when $R_1$ is an OH-protecting group, removing that protecting group by hydrolysis.

Within the scope of the present invention, transition metal salts are to be understood as being those salts which contain as metal component a transition metal of group VIII. Of the 9 metals in this group, namely Fe, Ru, Os, Co, Rh, Ir, Ni, Pd and Pt, there are preferred as metal components of the transition metal salts Co, Ni and Pd. Suitable transition metal salts are purely inorganic transition metal salts and also those which are complexed with organic ligands. Typical organic ligands are phosphines and organically substituted amines. Representative examples of suitable transition metal salts are $NiCl_2$, $CoCl_2$, [(phenyl)$_3$P]$_2$NiCl$_2$, [(phenyl)$_3$P]$_2$PdCl$_2$, [(phenyl)$_2$PCH$_2$]$_2$NiCl$_2$, [(phenyl)$_2$PCH$_2$]$_2$CoBr$_2$, [(phenyl)$_2$PCH$_2$CH$_2$CH$_2$P(phenyl)$_2$]NiCl$_2$, [(phenyl)$_2$PCH$_2$CH$_2$]$_2$NiCl$_2$ and [(cyclohexyl)$_3$P]$_2$NiCl$_2$.

The diaryl zinc compounds of formula III are either known or can be prepared analogously to known methods (N.I. Sheverdina et al., Doklady Akad. SSSR 155, 623 (1964); Engl.: 299).

Here and hereinafter, compounds of formula II in which G is a group a are designated IIa and those having the group b are designated IIb.

Compounds of formula IIa in which $R_2$ is methyl, ethyl, isopropyl or sec.-butyl and $R_1$ and E are as defined for formula II, and a process for the preparation thereof are known.

The compounds of the formula IIa are prepared by 13β-halogenation of a compound of formula

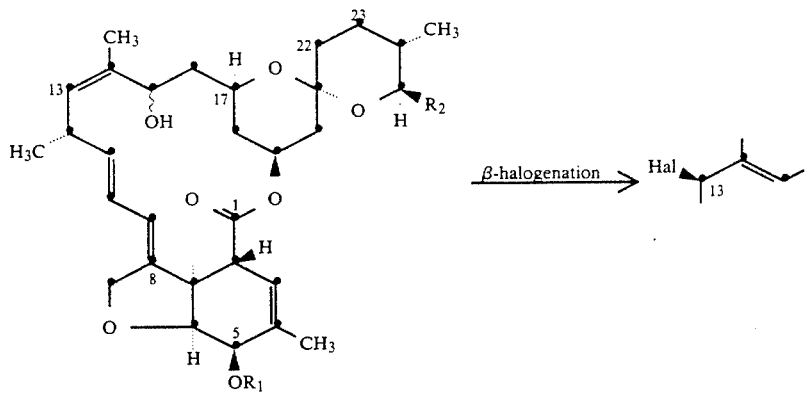

wherein $R_1$ and $R_2$ are as defined for formula I, with halogenating agents suitable for the introduction of halogen into the 13β-position. Presumably, in this reaction, after the initial halogenation of the 15—OH group, the resultant 15-Hal group surprisingly changes its position in an allylic rearrangement to the 13-position with shifting of the double bond to the 14,15-position.

Anhydrous solvents which do not contain OH groups are used in the above surprising reaction.

If compounds of formula IIa are desired wherein $R_1 = H$, halogenation must be effected with a compound of the formula II', the very reactive 5—OH group of which is protected.

Suitable protecting groups are the silyl and acyl groups indicated above in the definition of $R_1$ or e.g. a benzylether, methoxyethoxymethyl ether or dihydrofuran or dihydropyran radicals. These protecting groups can be introduced either into compounds of formula II' or at an earlier reaction stage and, on completion of the reaction, can be splitt off in conventional manner.

Suitable agents for the 13β-chlorination or 13β-bromination of compounds of formula II' are halogenating agents such as thionyl chloride ($SOCl_2$), phosphorus trichloride ($PCl_3$) or thionyl bromide ($SOBr_2$) and phosphorus tribromide ($PBr_3$) or a combination of triphenylphosphine and -bromine. The reaction temperatures are in the range from $-40°$ C. to $+10°$ C., preferably from $-25°$ C. to $0°$ C.

Suitable solvents are hydrocarbons, e.g. pentane, and chlorinated hydrocarbons, e.g. dichloromethane, which occur in the liquid state at these temperatures. The 13β-chlorination or 13β-bromination is preferably carried out in the presence of a base such as triethylamine, triethylenediamine, pyridine etc.

Suitable agents for the 13β-iodination of compounds of formula II' are a combination of iodine, triphenylphosphine ($=PPh_3$) and imidazole or a combination of triphenylphosphine and 2,4,5-triiodoimidazole, which combinations are conveniently employed in excess. This reaction can be carried out in hydrocarbons, e.g. hexane or toluene, or in halogenated hydrocarbons, e.g. dichloromethane, chloroform or chlorobenzene, at a temperature in the range from $-10°$ C. to $+60°$ C., preferably from $+10°$ C. to $+40°$ C.

The compounds of formula IIb

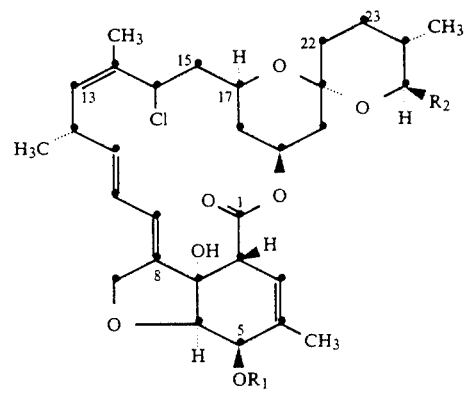

in which $R_1$ is hydrogen or an OH-protecting group; and
$R_2$ is methyl, ethyl, isopropyl or sec.-butyl, are novel and also constitute a further aspect of the present invention, as does the process for their preparation. The compounds of formula IIb are prepared by reacting a milbemycin of formula M with a chlorinating agent that brings about the formation of the corresponding 15-chloro-$\Delta^{13,14}$ derivative.

It is already known from EP 143 747 that reaction of milbemycins of formula M with hypochlorous acid (HOCl) or sulfuryl chloride ($SO_2Cl_2$) gives compounds of formula M'

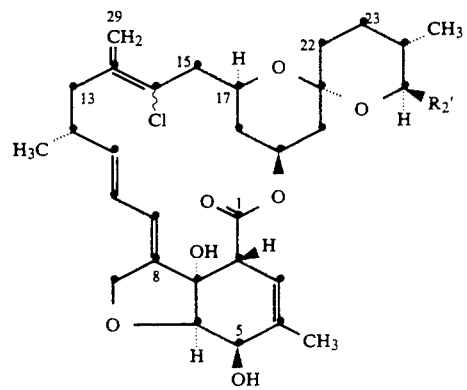

wherein $R_{2'}$ is as defined for formula M. This reaction constitutes a chlorination in the 15-position with the simultaneous formation of an exocyclic double bond in the 29-14-position.

It is also known that the chlorination of alkenyl and dialkenyl compounds and cyclohexylidene can be effected with tert.-butyl hypochlorite or chlorine (W. Sato et al., Chemistry Lett. 1982, 141-142; M. Yoshioka et al., Tetrahedron Lett. 21, 351-354).

None of the known processes, however, gives any indication of how it would be possible to obtain the compounds of formula IIb of the invention which have endocylic carbon-carbon double bonds.

It has been found that, surprisingly, compounds of formula IIb can be prepared by reacting a compound of formula M with tert.-butyl hypochlorite. This process also forms an aspect of the present invention.

The process is generally carried out in an inert solvent. Suitable solvents are, for example, ethers and ethereal compounds, such as dialkyl ethers (diethyl ether, diisopropyl ether, tert.-butylmethyl ether, dimethoxyethane, dioxane, tetrahydrofuran or anisole); halogenated hydrocarbons, such as, for example, chlorobenzene, methylene chloride or ethylene chloride; or sulfoxides, such as dimethyl sulfoxide, it also being possible for aromatic or aliphatic hydrocarbons, such as, for example, benzene, toluene, xylenes, petroleum ether, ligroin or cyclohexane, to be present.

The reaction is generally carried out in a temperature range of from $-50°$ C. to $+50°$ C., preferably at from $-10°$ C. to $+20°$ C.

A further process for the preparation of compounds of formula I comprises introducing the substituent "Ph" into corresponding 13-acyloxy-$\Delta^{14,15}$ derivatives or 15-acyloxy-$\Delta^{13,14}$ derivatives by reacting said derivatives with a triarylaluminum compound. This reaction can be carried out analogously to the method described in EP 189 159, which method also includes the preparation of the acylated starting compounds.

Accordingly, the present invention further relates to a process for the preparation of compounds of formula I, which comprises treating a compound of formula V

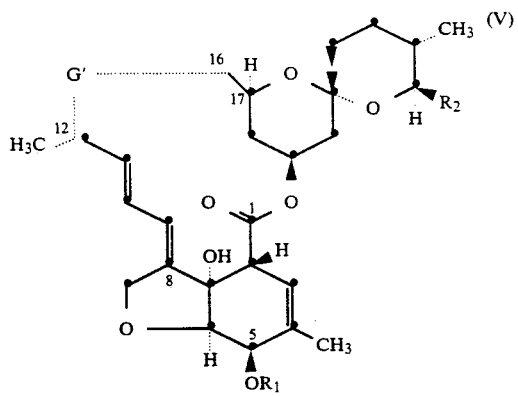

wherein G' is one of the groups a' or b'

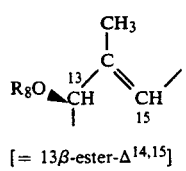

[= 13β-ester-$\Delta^{14,15}$]

or

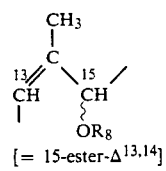

[= 15-ester-$\Delta^{13,14}$]

$R_8$ is an acyl group, $R_1$ is hydrogen or, preferably, a silyl group, and $R_2$ is as defined for formula I, with a triarylaluminum compound of formula VI $$Al(Ph)_3 \qquad (VI),$$

wherein Ph is as defined for formula I, and then, if free 5-hydroxy compounds are desired, removing the $R_1$-silyl group by hydrolysis.

The process is generally carried out in an inert solvent. Suitable solvents are, for example, ethers and ethereal compounds, such as dialkyl ethers (diethyl ether, diisopropyl ether, tert.-butylmethyl ether, dimethoxyethane, dioxane, tetrahydrofuran or anisole); halogenated hydrocarbons, such as, for example, chlorobenzene, methylene chloride or ethylene chloride; and aromatic or aliphatic hydrocarbons, such as, for example, benzene, toluene, xylenes, petroleum ether, ligroin or cyclohexane, may also be present.

It can be advantageous to carry out the reaction or partial steps thereof under a protective gas atmosphere (for example argon, helium or nitrogen) and/or in absolute solvents. If desired, intermediates may be isolated from the reaction mixture and, if desired, purified in customary manner, e.g. by washing, digestion, extraction, recrystallisation, chromatography, etc., before being further reacted. It is, however, also possible to dispense with such purification steps and carry them out only with corresponding end products.

The reaction is generally carried out in a temperature range of from $-100°$ C. to 100° C., preferably at from $-20°$ C. to $+60°$ C. The triarylaluminium compound of formula VI is added in an at least equimolar amount, in solid form or in an inert solvent, such as, for example, hexane, toluene or benzene, to a solution of the compound of formula V.

When the reaction is complete, the silyl protecting group can be removed again by treating the compounds of formula I with a dilute acid, such as, for example, with 1% p-toluenesulfonic acid in methanol or with an aqueous HF solution in acetonitrile in a temperature range of from $-20°$ C. to 50° C., preferably at from 0° C. to 30° C., or with pyridinium fluoride in pyridine.

Suitable acyl groups for $R_8$ are, for example, formyl, acetyl, benzoyl, ethoxycarbonyl or P(=O)(Oalkyl)$_2$, such as P(=O)(OEt)$_2$, alkylsulfonyl radicals, preferably lower alkylsulfonyl, especially mesyl, or, to a limited extent, also tetrahydropyranyl.

The 5-keto-milbemycins in which X is —C(O)—, which fall within the scope of formula I, can be obtained, for example, by treating compounds of formula I in which X is —CH(OH)— with a reagent suitable for the purpose of oxidation. Suitable oxidising agents are, for example, activated manganese dioxide, oxalyl chloride/dimethyl sulfoxide/triethylamine or chromium trioxide/pyridine. The Oppenauer oxidation also is a suitable process, in which compounds of formula I in which X is —CH(OH)— are reacted with a ketone, preferably cyclohexanone or acetone, in the presence of an aluminium alcoholate, preferably aluminium isopropanolate or aluminium tert.-butanolate.

The oxidation is advantageously carried out in an inert solvent. Suitable solvents are alkanes, such as, for example, hexane, heptane or octane, aromatic hydrocarbons, such as, for example, benzene, toluene or xylenes, or preferably chlorinated hydrocarbons, especially methylene chloride. The oxidation is advantageously carried out at temperatures of from $-80°$ C. to $+60°$ C., preferably from $-60°$ C. to $+30°$ C.

By reduction of compounds of formula I in which X is the —C(O)— group in a manner known per se, it is possible to obtain again those compounds in which X is the —CH(OH)— group. The reduction can be effected, for example, in accordance with the Meerwein-Ponndorf-Verley reduction using aluminium isopropanolate in isopropanol.

Compounds of formula I in which X is —C(=N—OR)— can be prepared, for example, by reacting compounds of formula I in which X is —C(O)— with hydroxylamine or a salt thereof and, if desired, subsequently introducing the substituent R, R having the meanings given for formula I with the exception of hydrogen, or by carrying out the reaction with a compound of formula $NH_2$—OR wherein R has the meanings given for formula I with the exception of hydrogen, or with a salt thereof. Suitable salts are, for example, salts of the above-mentioned amino compounds with sulfuric acid, nitric acid or, especially, hydrochloric acid. The reaction is advantageously carried out in a suitable solvent, for example a lower alkanol, such as methanol, ethanol, propanol; an ethereal compound, such as tetrahydrofuran or dioxane; an aliphatic carboxylic acid, such as acetic acid or propionic acid; water, or in mixtures of these solvents with one another or with other customary inert solvents. The reaction temperatures may vary within wide limits. Advantageously, a temperature in the range of, for example, from $+10°$ C. to $+100°$ C. is used. If hydroxylamine is used in the form of one of its salts, for example in the form of the hydrochloride, it is advantageous, in order to bind the acid, to add one of the bases customarily used for such purposes and, where necessary, to carry out the reaction in the presence of a water-binding agent, for example a molecular sieve. Suitable bases are organic and inorganic bases, e.g. tertiary amines such as trialkylamines (trimethylamine, triethylamine, tripropylamine etc.), pyridine and pyridine bases (4-dimethylaminopyridine, 4-pyrrolidylaminopyridine etc.), oxides, hydrides and hydroxides, carbonates and hydrogen carbonates of alkali metals and alkaline earth metals (CaO, BaO, NaOH, KOH, NaH, $Ca(OH)_2$, $KHCO_3$, $NaHCO_3$, $Ca(HCO_3)_2$, $K_2CO_3$, $Na_2CO_3$), and alkali metal acetates such as $CH_3COONa$ or $CH_3COOK$. Also suitable are alkali metal alcoholates such as $C_2H_5ONa$, $n$—$C_3H_7ONa$ etc.. Triethylamine is preferred.

The compounds of formula I are eminently suitable for controlling pests in and on animals and plants in all their development stages, especially ectoparasites that parasitise animals. These last-mentioned pests comprise, of the order Acarina, especially pests of the families Ixodidae, Dermanyssidae, Sarcoptidae, Psoroptidae; the orders Mallophaga; Siphonaptera, Anoplura (e.g. the Haemotopinidae family); and, of the order Diptera, especially pests of the families Muscidae, Calliphoridae, Oestridae, Tabanidae, Hippoboscidae and Gastrophilidae.

The compounds of formula I can also be used to control hygiene pests, especially those of the order Diptera comprising the families Sarcophagidae, Anophilidae, Culicidae; of the order Orthoptera, of the order Dictyoptera (e.g. the Blattidae family) and of the order Hymenoptera (e.g. the Formicidae family).

The compounds of formula I also have a lasting action against mites and insects that are parasites of plants. When used to control spider mites of the order Acarina, they are effective against eggs, nymphs and adults of Tetranychidae (Tetranychus spp. and Panonychus spp.).

They are highly effective against sucking insects of the order Homoptera, especially against pests of the families Aphididae, Delphacidae, Cicadellidae, Psyllidae, Loccidae, Diaspididae and Eriophydidae (e.g. the rust mite on citrus fruit); of the orders Hemiptera; Heteroptera and Thysanoptera; and against plant-feeding insects of the orders Lepidoptera, Coleoptera, Diptera and Orthoptera.

They are also suitable as soil insecticide against soil pests.

The compounds of formula I are therefore effective against all development stages of sucking and feeding insects in crops such as cereals, cotton, rice, maize, soybeans, potatoes, vegetables, fruit, tobacco, hops, citrus fruit, avocados and others.

The compounds of formula I are also effective against plant nematodes of the species Meloidogyne, Heterodera, Pratylenchus, Ditylenchus, Radopholus, Rizoglyphus and others.

The compounds are also effective against helminths in all stages of development, among which the endoparasitic nematodes can cause severe diseases in mammals and fowl, for example sheep, pigs, goats, cattle, horses, donkeys, dogs, cats, guinea pigs, cage birds. Typical nematodes having this indication are: Haemonchus, Trichostrongylus, Ostertagia, Nematodirus, Cooperia, Ascaris, Bunostomum, Oesophagostomum, Charbertia, Trichuris, Strongylus, Trichomena, Dictyocaulus, Capillaria, Heterakis, Toxocara, Ascaridia, Oxyuris, Ancylostoma, Uncinaria, Toxascaris and Parascaris. A particular advantage of the compounds of formula I is their effectiveness against parasites that are resistant to benzimidazole-based active substances.

Certain species of the genera Nematodirus, Cooperia and Oesophagostomum attack the intestinal tract of the host animals, whereas others of the genera Haemonchus and Ostertagia parasitise the stomach and those of the genus Dictyocaulus the lung tissue. Parasites of the families Filariidae and Setariidae are found in internal cell tissue and in organs, for example in the heart, blood vessels, lymph vessels and in the subcutaneous tissue. In this connection, particular mention should be made of the dog heartworm, *Dirofilaria immitis*. The compounds of formula I are highly effective against these parasites.

The compounds of formula I are also suitable for controlling pathogenic parasites in humans, among which parasites there may be mentioned as typical representatives occurring in the alimentary tract those of the genera Ancylostoma, Necator, Ascaris, Strongyloides, Trichinella, Capillaria, Trichuris and Enterobius. The compounds of this invention are also effective against parasites of the genera Wuchereria, Brugia, Onchocerca and Loa of the Filariidae family, which occur in the blood, in tissue and in various organs, and, in addition, against Dracunculus and parasites of the genera Strongyloides and Trichinella which infest, in particular, the gastro-intestinal tract.

The compounds of formula I are used in unmodified form or, preferably, together with the adjuvants conventionally employed in the art of formulation, and are therefore formulated in known manner e.g. to emulsifiable concentrates, directly sprayable or dilutable solutions, dilute emulsions, wettable pwders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The compounds of formula I are administered to warm-blooded animals in amounts of from 0.01 to 10 mg/kg of body weight. When the compounds of formula I, or corresponding compositions, are used for controlling endoparasitic nematodes, cestodes and trematodes in domestic animals and productive livestock, such as cattle, sheep, goats, cats and dogs, they can be administered to the animals both in the form of a single dose and repeatedly, the individual dosage amounts being preferably from 0.1 to 10 mg per kg of body weight depending on the species of animal. By protracted administration, a better effect is achieved in some cases or lower overall doses may suffice. The active ingredient, or the composition containing it, can also be added to the feeds or drinks. The ready-prepared feed preferably contains the active ingredient combinations in a concentration of from 0.005 to 0.1% by weight. The compositions may be administered to the animals perorally in the form of solutions, emulsions, suspensions, powders, tablets, boli or capsules. Provided the physical and toxicological properties of the solutions or emulsions permit, the compounds of formula I, or the compositions containing them, can also be administered to animals, for example, by subcutaneous injection or intraruminally, or may be applied to the bodies of the animals by the pour-on method. It is further possible to administer the active ingredient to the animals by means of licks (salt licks) or mollasses blocks. Over enclosed crop areas they are advantageously applied in amounts of from 10 g to 1000 g per hectare. They are also used in pens, paddocks, stalls or other livestock buildings.

The formulations, i.e. the compositions, preparations or mixtures containing the compound (active ingredient) of formula I are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents, such as N-methyl-2-pyrrolidone, dimethyl sulfoxide or dimethylformamide, and also vegetable oils or epoxidised vegetable oils, such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide; or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of poloxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described inter alia in the following publication:"1986 International McCutcheon's Emulsifiers and Detergents", The Manufacturing Confectioner Publishing Co., Glen Rock, New Jersey, USA.

The pesticidal compositions usually contain from 0.01 to 95%, preferably from 0.1 to 80%, of a compound of formula I, from 5 to 99.99% of a solid or liquid adjuvant, and from 0 to 25%, preferably from 0.1 to 25%, of a surfactant.

Whereas commercial products will preferably be formulated as concentrates, the end user will normally employ dilute formulations having an active ingredient content of from 1 to 10,000 ppm.

The present invention further relates, therefore, to pesticides that contain at least one compound of formula I as active ingredient, together with conventional carriers and/or distributing agents.

The compositions may also contain further auxiliaries such as stabilisers, antifoams, viscosity regulators, binders, tackifiers as well as fertilisers or other active ingredients for obtaining special effects.

PREPARATION EXAMPLES

Example A1: Preparation of 5-O-tert.-butyldimethylsilyl-15-chloro-$\Delta^{13,14}$-milbemycin $A_4$ With stirring at $-10°$ C., 200 µl (182 mg; 1.52 mmol) of tert.-butyl hypochlorite are added to a solution of 1 g (1.52 mmol) of 5-O-tert.-butyldimethylsilyl-milbemycin $A_4$ in 2 ml of dichloromethane and 8 ml of diethyl ether. After stirring at room temperature for 1 hour, the solvent is removed by evaporation. Chromatography of the crude product (80 g of silica gel; eluant: ethyl acetate/hexane 1:16) affords (in addition to 321 mg of 5-O-tert.-butyldimethylsilyl-15-chloro-$\Delta^{14,29}$-milbemycin $A_4$) 486 mg of the title compound, 5-O-tert.-butyldimethylsilyl-15-chloro-$\Delta^{13,14}$-milbemycin $A_4$.

$^1$H-NMR (300 MHz, CDCl$_3$, TMS), 3.05 ppm (m) ($C_{12}H$), 4.42 ppm (m) ($C_{15}H$), 4.87 ppm (m) ($C_{19}H$), 5.23 ppm (d, J=10 Hz) ($C_{13}H$).

Mass spectrum FD m/e: 690 (M+, $C_{38}H_{59}ClO_7Si$).

Example A2: Preparation of 15-chloro-$\Delta^{13,14}$-milbemycin $A_4$

With stirring at 0° C., 0.049 ml (45 mg; 0.412 mmol) of tert.-butyl hypochlorite is added to a solution of 203 mg (0.375 mmol) of milbemycin $A_4$ in 5 ml of diethyl ether. After stirring at room temperature for 2 hours, the solvent is removed by evaporation. Chromatography of the crude product (20 g of silica gel; eluant: acetone/dichloromethane 1:50) affords (in addition to 55 mg of 15-chloro-$\Delta^{14,29}$-milbemycin $A_4$) 97 mg of the title compound, 15-chloro-$\Delta^{13,14}$-milbemycin $A_4$.

$^1$H-NMR (300 MHz, CDCl$_3$, TMS), 3.06 ppm (m) ($C_{12}H$), 4.39 ppm (dd, J=4 and 12 Hz) ($C_{15}$ H), 4.87 ppm (m) ($C_{19}H$), 5.2 ppm (m) ($C_{13}H$).

Mass spectrum FD m/e: 576 (M+, $C_{32}H_{45}ClO_7$)

Example P1: Preparation of 13$\beta$-phenyl-milbemycin $A_4$ a) Preparation of diphenyl zinc:

With stirring at 0° C. under an argon atmosphere, 6 ml (12 mmol) of a 2M solution of phenyl magnesium chloride in tetrahydrofuran are added to 818 mg (6 mmol) of zinc chloride. After stirring at room temperature for 16 hours, 5 ml of toluene are added thereto. The solution is stirred for 10 minutes and then kept without being stirred.

b) Preparation of 5-O-tert.-butyldimethylsilyl-13$\beta$-phenyl-milbemycin $A_4$:

With stirring at room temperature under an argon atmosphere, 4 ml of the solution obtained in a) are added to a solution of 150 mg (0.204 mmol) of 5-O-tert.-butyldimethylsilyl-13$\beta$-bromo-milbemycin $A_4$ and 13.4 mg (0.020 mmol) of bis-(triphenylphosphine)-nickel(II) chloride [(dichlorobis(triphenylphosphine)-nickel; NiCl$_2$ (phenyl$_3$P)$_2$] in 1 ml of toluene. After 10 minutes at room temperature, the batch is worked up with ether, 2M sodium potassium tartrate solution and kieselguhr. Chromatography of the crude product (silica gel 20 g; eluant: ethyl acetate/hexane 1:12) and HPLC (eluant: diethyl ether/hexane 1:6) affords 38 mg of 5-O-tert.-butyldimethylsilyl-13$\beta$-phenyl-milbemycin $A_4$.

$^1$H-NMR (300 MHz, CDCl$_3$, TMS), 2.94 ppm (m) ($C_{12}H$), 3.07 ppm (d, J=10 Hz) $C_{13}H$), 7.15–7.30 ppm (m) (phenyl).

Mass spectrum (FD) m/e: 732 (M+, $C_{44}H_{64}O_7Si$).

c) Preparation of 13$\beta$-phenyl-milbemycin $A_4$:

34 mg (0.046 mmol) of 5-O-tert.-butyldimethylsilyl-13$\beta$-phenyl-milbemycin $A_4$ are treated with 2 ml of a 40% aqueous solution of HF in acetonitrile (5:95) for 2 hours at room temperature. Working up in diethyl ether with 5% aqueous NaHCO$_3$ solution and chromatography on silica gel (ethyl acetate/hexane 1:2) yields 27 mg of 13$\beta$-phenyl-milbemycin $A_4$.

$^1$H-NMR (300 MHz, CDCl$_3$, TMS), 2.84 ppm (m) ($C_{12}H$), 3.10 ppm (d, J=10 Hz) ($C_{13}H$), 7.16–7.35 ppm (m) (phenyl).

Mass spectrum (FD) m/e: 618 (M+, $C_{38}H_{50}O_7$)

Example P2: Preparation of 13$\beta$-(4-biphenylyl)-milbemycin $A_4$

13$\beta$-(4-biphenylyl)-milbemycin $A_4$ is prepared analogously to Example P1 but with 5-O-tert.-butyldimethylsilyl-15-chloro-$\Delta^{13,14}$-milbemycin $A_4$ instead of 5-O-tert.-butyldimethylsilyl-13$\beta$-bromo-milbemycin $A_4$.

$^1$H-NMR (300 MHz, CDCl$_3$, TMS), 2.93 ppm (m) ($C_{12}H$), 3.17 ppm (d, J=10 Hz) ($C_{13}H$), 7.25–7.61 ppm (m) (biphenyl).

Mass spectrum (FD) m/e: 694 ($C_{44}H_{54}O_7$).

Example P3: Preparation of 13$\beta$-(3-methoxyphenyl)-milbemycin $A_4$

13$\beta$-(3-methoxyphenyl)-milbemycin $A_4$ is prepared analogously to Example P2.

$^1$H-NMR (300 MHz, CDCl$_3$, TMS), 2.83 ppm (m) ($C_{12}H$), 3.10 ppm (d, J=10 Hz) ($C_{13}H$), 3.83 ppm (s) ($CH_3O$), 6.74–6.89 ppm (m) (aromatic).

Mass spectrum (FD) m/e: 648 ($C_{39}H_{52}O_8$).

The following compounds also are prepared analogously to the methods described above:

Example P4: 13β-(3,4-dimethoxyphenyl)-milbemycin A₄

1H-NMR (300 MHz, CDCl₃, TMS), 2.80 ppm (m) (C₁₂H), 3.06 ppm (d, J=10 Hz) (C₁₃H), 3.86 ppm (s) (CH₃O), 3.88 ppm (s) (CH₃O), 6.70–6.83 ppm (m) (aromatic).

Mass spectrum (FD) m/e: 678 (C₄₀H₅₄O₉).

Example P5: 13β-(4-phenoxyphenyl)-milbemycin A₄

¹H-NMR (300 MHz, CDCl₃, TMS), 2.80 ppm (m) (C₁₂H), 3.07 ppm (d, J=10 Hz) (C₁₃H), 6.88–7.34 ppm (m) (aromatic).

Mass spectrum (FD) m/e: 710 (C₄₄H₅₄O₈).

Example P6: 13β-(2-methylphenyl)-milbemcin A₄

¹H-NMR (300 MHz, CDCl₃, TMS), 2.91 ppm (m) (C₁₂H), 3.36 ppm (d, J=10 Hz) (C₁₃H), 7.08–7.30 (m) (aromatic).

Mass spectrum (FD) m/e: 632 (C₃₉H₅₂O₇).

Example P7: 13β-(4-methylphenyl)-milbemycin A₄

¹H-NMR (300 MHz, CDCl₃, TMS), 2.84 ppm (m) (C₁₂H), 3.08 ppm (d, J=10 Hz) (C₁₃H), 7.27 ppm (m) (aromatic).

Mass spectrum (FD) m/e: 632 (C₃₉H₅₂O₇).

Example P8: 13β-(3-methylphenyl)-milbemycin A₄

1H-NMR (300 MHz, CDCl₃, TMS), 2.33 ppm (s) (CH₃-aromatic), 2.86 ppm (m) (C₁₂H), 3.08 ppm (d, J=10 Hz) (C₁₃H), 6.99–7.27 ppm (m) (aromatic).

Mass spectrum (FD) m/e: 632 (C₃₉H₅₂O₇).

Example P9: 13β-(4-methoxyphenyl)-milbemycin A₄

¹H-NMR (300 MHz, CDCl₃, TMS), 2.81 ppm (m) (C₁₂H), 3.07 ppm (d, J=10 Hz) (C₁₃H), 3.79 ppm (s) (CH₃O), 6.84 ppm (d, J=8 Hz) and 7.12 ppm (d, J=8 Hz) (aromatic).

Mass spectrum (FD) m/e: 648 (C₃₉H₅₂O₈).

Example P10: 13β-(2-methoxyphenyl)-milbemycin A₄

¹H-NMR (300 MHz, CDCl₃, TMS), 2.83 ppm (m) (C₁₂H), 3.81 ppm (s) (CH₃O), 6.83–7.28 ppm (m) (aromatic).

Example P11: 13β-(3-biphenylyl)-milbemycin A₄

¹H-NMR (300 MHz, CDCl₃, TMS), 2.94 ppm (m) (C₁₂H), 3.19 ppm (d, J=10 Hz) (C₁₃H), 3.98 ppm (d, J=6 Hz) (C₆H), 7.17–7.60 ppm (m) (aromatic).

Example P12: 13β-phenyl-milbemycin A₃

¹H-NMR (300 MHz, CDCl₃, TMS), 2.77 ppm (m) (C₁₂H), 3.01 ppm (d, J=10 Hz) (C₁₃H), 3.18 ppm (m) (C₂₅H), 7.09–7.23 ppm (m) (aromatic).

The following compounds of formula I, together with compounds of the preceding Examples, are also prepared analogously to the described procedures:

TABLE 1

Typical representatives of compounds of formula I wherein X is —CH(OR₁)— and R₁ is hydrogen.

| comp. no. | R₂ | Ph |
|---|---|---|
| 1.1 | CH₃ | 2-methylphenyl |
| 1.2 | C₂H₅ | 2-methylphenyl |
| 1.3 | C₃H₇-iso | 2-methylphenyl |
| 1.4 | C₄H₉-sec. | 2-methylphenyl |
| 1.5 | CH₃ | 4-methoxyphenyl |
| 1.6 | C₂H₅ | 4-methoxyphenyl |
| 1.7 | C₃H₇-iso | 4-methoxyphenyl |
| 1.8 | C₄H₉-sec. | 4-methoxyphenyl |
| 1.9 | CH₃ | 2,3-dimethylphenyl |
| 1.10 | C₂H₅ | 2,3-dimethylphenyl |
| 1.11 | C₃H₇-iso | 2,3-dimethylphenyl |
| 1.12 | C₄H₉-sec. | 2,3-dimethylphenyl |
| 1.13 | CH₃ | 3-(2-methoxyethoxy)-phenyl |
| 1.14 | C₂H₅ | 3-(2-methoxyethoxy)-phenyl |
| 1.15 | C₃H₇-iso | 3-(2-methoxyethoxy)-phenyl |
| 1.16 | C₄H₉-sec. | 3-(2-methoxyethoxy)-phenyl |
| 1.17 | CH₃ | phenyl |
| 1.18 | C₂H₅ | phenyl |
| 1.19 | C₃H₇-iso | phenyl |
| 1.20 | C₄H₉-sec. | phenyl |
| 1.21 | CH₃ | 2-n-butylphenyl |
| 1.22 | C₂H₅ | 2-n-butylphenyl |
| 1.23 | C₃H₇-iso | 2-n-butylphenyl |
| 1.24 | C₄H₉-sec. | 2-n-butylphenyl |
| 1.25 | CH₃ | 3,4-dimethoxyphenyl |
| 1.26 | C₂H₅ | 3,4-dimethoxyphenyl |
| 1.27 | C₃H₇-iso | 3,4-dimethoxyphenyl |
| 1.28 | C₄H₉-sec. | 3,4-diemthoxyphenyl |
| 1.29 | CH₃ | 4-isopropylphenyl |
| 1.30 | C₂H₅ | 4-isopropylphenyl |
| 1.31 | C₃H₇-iso | 4-isopropylphenyl |
| 1.32 | C₄H₉-sec. | 4-isopropylphenyl |
| 1.33 | CH₃ | 4-(ethoxymethyl)-phenyl |
| 1.34 | C₂H₅ | 4-(ethoxymethyl)-phenyl |
| 1.35 | C₃H₇-iso | 4-(ethoxymethyl)-phenyl |
| 1.36 | C₄H₉-sec. | 4-(ethoxymethyl)-phenyl |
| 1.37 | CH₃ | 4-methylphenyl |
| 1.38 | C₂H₅ | 4-methylphenyl |
| 1.39 | C₃H₇-iso | 4-methylphenyl |
| 1.40 | C₄H₉-sec. | 4-methylphenyl |
| 1.41 | CH₃ | 2-n-propoxyphenyl |
| 1.42 | C₂H₅ | 2-n-propoxyphenyl |
| 1.43 | C₃H₇-iso | 2-n-propoxyphenyl |
| 1.44 | C₄H₉-sec. | 2-n-propoxyphenyl |
| 1.45 | CH₃ | 2,3,5,6-tetramethoxyphenyl |
| 1.46 | C₂H₅ | 2,3,5,6-tetramethoxyphenyl |
| 1.47 | C₃H₇-iso | 2,3,5,6-tetramethoxyphenyl |
| 1.48 | C₄H₉-sec. | 2,3,5,6-tetramethoxyphenyl |
| 1.49 | CH₃ | 3-vinylphenyl |
| 1.50 | C₂H₅ | 3-vinylphenyl |
| 1.51 | C₃H₇-iso | 3-vinylphenyl |
| 1.52 | C₄H₉-sec. | 3-vinylphenyl |
| 1.53 | CH₃ | 4-n-propylphenyl |
| 1.54 | C₂H₅ | 4-n-propylphenyl |
| 1.55 | C₃H₇-iso | 4-n-propylphenyl |
| 1.56 | C₄H₉-sec. | 4-n-propylphenyl |
| 1.57 | CH₃ | 3-ethoxyphenyl |
| 1.58 | C₂H₅ | 3-ethoxyphenyl |
| 1.59 | C₃H₇-iso | 3-ethoxyphenyl |
| 1.60 | C₄H₉-sec. | 3-ethoxyphenyl |
| 1.61 | CH₃ | 2-ethylphenyl |
| 1.62 | C₂H₅ | 2-ethylphenyl |
| 1.63 | C₃H₇-iso | 2-ethylphenyl |
| 1.64 | C₄H₉-sec. | 2-ethylphenyl |
| 1.65 | CH₃ | 2-methyl-4-methoxyphenyl |
| 1.66 | C₂H₅ | 2-methyl-4-methoxyphenyl |
| 1.67 | C₃H₇-iso | 2-methyl-4-methoxyphenyl |
| 1.68 | C₄H₉-sec. | 2-methyl-4-methoxyphenyl |
| 1.69 | CH₃ | 2-(methoxymethoxy)-phenyl |
| 1.70 | C₂H₅ | 2-(methoxymethoxy)-phenyl |
| 1.71 | C₃H₇-iso | 2-(methoxymethoxy)-phenyl |
| 1.72 | C₄H₉-sec. | 2-(methoxymethoxy)-phenyl |
| 1.73 | CH₃ | 4-ethylphenyl |
| 1.74 | C₂H₅ | 4-ethylphenyl |
| 1.75 | C₃H₇-iso | 4-ethylphenyl |
| 1.76 | C₄H₉-sec. | 4-ethylphenyl |
| 1.77 | CH₃ | 2,4-dimethoxyphenyl |
| 1.78 | C₂H₅ | 2,4-dimethoxyphenyl |
| 1.79 | C₃H₇-iso | 2,4-dimethoxyphenyl |
| 1.80 | C₄H₉-sec. | 2,4-dimethoxyphenyl |
| 1.81 | CH₃ | 3-(2-methoxyethyl)-phenyl |
| 1.82 | C₂H₅ | 3-(2-methoxyethyl)-phenyl |

TABLE 1-continued

Typical representatives of compounds of formula I wherein X is —CH(OR$_1$)— and R$_1$ is hydrogen.

| comp. no. | R$_2$ | Ph |
|---|---|---|
| 1.83 | C$_3$H$_7$-iso | 3-(2-methoxyethyl)-phenyl |
| 1.84 | C$_4$H$_9$-sec. | 3-(2-methoxyethyl)-phenyl |
| 1.85 | CH$_3$ | 4-tert.-butylphenyl |
| 1.86 | C$_2$H$_5$ | 4-tert.-butylphenyl |
| 1.87 | C$_3$H$_7$-iso | 4-tert.-butylphenyl |
| 1.88 | C$_4$H$_9$-sec. | 4-tert.-butylphenyl |
| 1.89 | CH$_3$ | 2-methoxyphenyl |
| 1.90 | C$_2$H$_5$ | 2-methoxyphenyl |
| 1.91 | C$_3$H$_7$-iso | 2-methoxyphenyl |
| 1.92 | C$_4$H$_9$-sec. | 2-methoxyphenyl |
| 1.93 | CH$_3$ | 2,4,6-trimethylphenyl |
| 1.94 | C$_2$H$_5$ | 2,4,6-trimethylphenyl |
| 1.95 | C$_3$H$_7$-iso | 2,4,6-trimethylphenyl |
| 1.96 | C$_4$H$_9$-sec. | 2,4,6-trimethylphenyl |
| 1.97 | CH$_3$ | 4-(2-n-propoxyethoxy)-phenyl |
| 1.98 | C$_2$H$_5$ | 4-(2-n-propoxyethoxy)-phenyl |
| 1.99 | C$_3$H$_7$-iso | 4-(2-n-propoxyethoxy)-phenyl |
| 1.100 | C$_4$H$_9$-sec. | 4-(2-n-propoxyethoxy)-phenyl |
| 1.101 | CH$_3$ | 3-n-propylphenyl |
| 1.102 | C$_2$H$_5$ | 3-n-propylphenyl |
| 1.103 | C$_3$H$_7$-iso | 3-n-propylphenyl |
| 1.104 | C$_4$H$_9$-sec. | 3-n-propylphenyl |
| 1.105 | CH$_3$ | 4-allylphenyl |
| 1.106 | C$_2$H$_5$ | 4-allylphenyl |
| 1.107 | C$_3$H$_7$-iso | 4-allylphenyl |
| 1.108 | C$_4$H$_9$-sec. | 4-allylphenyl |
| 1.109 | CH$_3$ | 3,4-dimethylphenyl |
| 1.110 | C$_2$H$_5$ | 3,4-dimethylphenyl |
| 1.111 | C$_3$H$_7$-iso | 3,4-dimethylphenyl |
| 1.112 | C$_4$H$_9$-sec. | 3,4-dimethylphenyl |
| 1.113 | CH$_3$ | 2-ethoxyphenyl |
| 1.114 | C$_2$H$_5$ | 2-ethoxyphenyl |
| 1.115 | C$_3$H$_7$-iso | 2-ethoxyphenyl |
| 1.116 | C$_4$H$_9$-sec. | 2-ethoxyphenyl |
| 1.117 | CH$_3$ | 3-n-propoxyphenyl |
| 1.118 | C$_2$H$_5$ | 3-n-propoxyphenyl |
| 1.119 | C$_3$H$_7$-iso | 3-n-propoxyphenyl |
| 1.120 | C$_4$H$_9$-sec. | 3-n-propoxyphenyl |
| 1.121 | CH$_3$ | 2-isopropylphenyl |
| 1.122 | C$_2$H$_5$ | 2-isopropylphenyl |
| 1.123 | C$_3$H$_7$-iso | 2-isopropylphenyl |
| 1.124 | C$_4$H$_9$-sec. | 2-isopropylphenyl |
| 1.125 | CH$_3$ | 2,3-dimethoxyphenyl |
| 1.126 | C$_2$H$_5$ | 2,3-dimethoxyphenyl |
| 1.127 | C$_3$H$_7$-iso | 2,3-dimethoxyphenyl |
| 1.128 | C$_4$H$_9$-sec. | 2,3-dimethoxyphenyl |
| 1.129 | CH$_3$ | 3-methylphenyl |
| 1.130 | C$_2$H$_5$ | 3-methylphenyl |
| 1.131 | C$_3$H$_7$-iso | 3-methylphenyl |
| 1.132 | C$_4$H$_9$-sec. | 3-methylphenyl |
| 1.133 | CH$_3$ | 2-(ethoxymethoxy)-phenyl |
| 1.134 | C$_2$H$_5$ | 2-(ethoxymethoxy)-phenyl |
| 1.135 | C$_3$H$_7$-iso | 2-(ethoxymethoxy)-phenyl |
| 1.136 | C$_4$H$_9$-sec. | 2-(ethoxymethoxy)-phenyl |
| 1.137 | CH$_3$ | 3-isobutylphenyl |
| 1.138 | C$_2$H$_5$ | 3-isobutylphenyl |
| 1.139 | C$_3$H$_7$-iso | 3-isobutylphenyl |
| 1.140 | C$_4$H$_9$-sec. | 3-isobutylphenyl |
| 1.141 | CH$_3$ | 4-n-propoxyphenyl |
| 1.142 | C$_2$H$_5$ | 4-n-propoxyphenyl |
| 1.143 | C$_3$H$_7$-iso | 4-n-propoxyphenyl |
| 1.144 | C$_4$H$_9$-sec. | 4-n-propoxyphenyl |
| 1.145 | CH$_3$ | 2,4-dimethylphenyl |
| 1.146 | C$_2$H$_5$ | 2,4-dimethylphenyl |
| 1.147 | C$_3$H$_7$-iso | 2,4-dimethylphenyl |
| 1.148 | C$_4$H$_9$-sec. | 2,4-dimethylphenyl |
| 1.149 | CH$_3$ | 3-methoxyphenyl |
| 1.150 | C$_2$H$_5$ | 3-methoxyphenyl |
| 1.151 | C$_3$H$_7$-iso | 3-methoxyphenyl |
| 1.152 | C$_4$H$_9$-sec. | 3-methoxyphenyl |
| 1.153 | C$_3$H$_7$-iso | 4-(tert.-butoxymethyl)-phenyl |
| 1.154 | C$_4$H$_9$-sec. | 4-(tert.-butoxymethyl)-phenyl |
| 1.155 | CH$_3$ | 4-(tert.-butoxymethyl)-phenyl |
| 1.156 | C$_2$H$_5$ | 4-(tert.-butoxymethyl)-phenyl |
| 1.157 | CH$_3$H$_7$-iso | 3-isopropylphenyl |
| 1.158 | C$_4$H$_9$-sec. | 3-isopropylphenyl |
| 1.159 | CH$_3$ | 3-isopropylphenyl |
| 1.160 | C$_2$H$_5$ | 3-isopropylphenyl |
| 1.161 | CH$_3$H$_7$-iso | 3,5-dimethoxyphenyl |
| 1.162 | C$_4$H$_9$-sec. | 3,5-dimethoxyphenyl |
| 1.163 | C$_3$ | 3,5-dimethoxyphenyl |
| 1.164 | C$_2$H$_5$ | 3,5-dimethoxyphenyl |
| 1.165 | CH$_3$H$_7$-iso | 2-n-propylphenyl |
| 1.166 | C$_4$H$_9$-sec. | 2-n-propylphenyl |
| 1.167 | C$_3$ | 2-n-propylphenyl |
| 1.168 | C$_2$H$_5$ | 2-n-propylphenyl |
| 1.169 | CH$_3$H$_7$-iso | 2-(methoxymethyl)-phenyl |
| 1.170 | C$_4$H$_9$-sec. | 2-(methoxymethyl)-phenyl |
| 1.171 | C$_3$ | 2-(methoxymethyl)-phenyl |
| 1.172 | C$_2$H$_5$ | 2-(methoxymethyl)-phenyl |
| 1.173 | CH$_3$H$_7$-iso | 4-ethoxyphenyl |
| 1.174 | C$_4$H$_9$-sec. | 4-ethoxyphenyl |
| 1.175 | C$_3$ | 4-ethoxyphenyl |
| 1.176 | C$_2$H$_5$ | 4-ethoxyphenyl |
| 1.177 | CH$_3$H$_7$-iso | 2,4,6-trimethoxyphenyl |
| 1.178 | C$_4$H$_9$-sec. | 2,4,6-trimethoxyphenyl |
| 1.179 | C$_3$ | 2,4,6-trimethoxyphenyl |
| 1.180 | C$_2$H$_5$ | 2,4,6-trimethoxyphenyl |
| 1.181 | CH$_3$H$_7$-iso | 3-ethylphenyl |
| 1.182 | C$_4$H$_9$-sec. | 3-ethylphenyl |
| 1.183 | C$_3$ | 3-ethylphenyl |
| 1.184 | C$_2$H$_5$ | 3-ethylphenyl |
| 1.185 | CH$_3$ | 3,5-dimethylphenyl |
| 1.186 | C$_2$H$_5$ | 3,5-dimethylphenyl |
| 1.187 | C$_3$H$_7$-iso | 3,5-dimethylphenyl |
| 1.188 | C$_4$H$_9$-sec. | 3,5-dimethylphenyl |
| 1.189 | CH$_3$ | 3-methoxy-4-methylphenyl |
| 1.190 | C$_2$H$_5$ | 3-methoxy-4-methylphenyl |
| 1.191 | C$_3$H$_7$-iso | 3-methoxy-4-methylphenyl |
| 1.192 | C$_4$H$_9$-sec. | 3-methoxy-4-methylphenyl |
| 1.193 | CH$_3$ | 4-(3-methyl-4-methoxyphenoxy)-phenyl |
| 1.194 | C$_2$H$_5$ | 4-(3-methyl-4-methoxyphenoxy)-phenyl |
| 1.195 | C$_3$H$_7$-iso | 4-(3-methyl-4-methoxyphenoxy)-phenyl |
| 1.196 | C$_4$H$_9$-sec. | 4-(3-methyl-4-methoxyphenoxy)-phenyl |
| 1.197 | CH$_3$ | 3-biphenylyl |
| 1.198 | C$_2$H$_5$ | 3-biphenylyl |
| 1.199 | C$_3$H$_7$-iso | 3-biphenylyl |
| 1.200 | C$_4$H$_9$-sec. | 3-biphenylyl |
| 1.201 | CH$_3$ | 2'-ethoxy-3-biphenylyl |
| 1.202 | C$_2$H$_5$ | 2'-ethoxy-3-biphenylyl |
| 1.203 | C$_3$H$_7$-iso | 2'-ethoxy-3-biphenylyl |
| 1.204 | C$_4$H$_9$-sec. | 2'-ethoxy-3-biphenylyl |
| 1.205 | CH$_3$ | 3',4',5'-trimethoxy-4-biphenylyl |
| 1.206 | C$_2$H$_5$ | 3',4',5'-trimethoxy-4-biphenylyl |
| 1.207 | C$_3$H$_7$-iso | 3',4',5'-trimethoxy-4-biphenylyl |
| 1.208 | C$_4$H$_9$-sec. | 3',4',5'-trimethoxy-4-biphenylyl |
| 1.209 | CH$_3$ | 3-phenoxyphenyl |
| 1.210 | C$_2$H$_5$ | 3-phenoxyphenyl |
| 1.211 | C$_3$H$_7$-iso | 3-phenoxyphenyl |
| 1.212 | C$_4$H$_9$-sec. | 3-phenoxyphenyl |
| 1.213 | CH$_3$ | 4'-methoxy-3-biphenylyl |
| 1.214 | C$_2$H$_5$ | 4'-methoxy-3-biphenylyl |
| 1.215 | C$_3$H$_7$-iso | 4'-methoxy-3-biphenylyl |
| 1.216 | C$_4$H$_9$-sec. | 4'-methoxy-3-biphenylyl |
| 1.217 | CH$_3$ | 4-(3-methoxyphenoxy)-phenyl |
| 1.218 | C$_2$H$_5$ | 4-(3-methoxyphenoxy)-phenyl |
| 1.219 | C$_3$H$_7$-iso | 4-(3-methoxyphenoxy)-phenyl |
| 1.220 | C$_4$H$_9$-sec. | 4-(3-methoxyphenoxy)-phenyl |
| 1.221 | CH$_3$ | 2'-methyl-4-biphenylyl |
| 1.222 | C$_2$H$_5$ | 2'-methyl-4-biphenylyl |
| 1.223 | C$_3$H$_7$-iso | 2'-methyl-4-biphenylyl |
| 1.224 | C$_4$H$_9$-sec. | 2'-methyl-4-biphenylyl |
| 1.225 | CH$_3$ | 3'-n-propoxy-3-biphenylyl |
| 1.226 | C$_2$H$_5$ | 3'-n-propoxy-3-biphenylyl |
| 1.227 | C$_3$H$_7$-iso | 3'-n-propoxy-3-biphenylyl |
| 1.228 | C$_4$H$_9$-sec. | 3'-n-propoxy-3-biphenylyl |
| 1.229 | CH$_3$ | 4-(4-methylphenoxy)-phenyl |
| 1.230 | C$_2$H$_5$ | 4-(4-methylphenoxy)-phenyl |
| 1.231 | C$_3$H$_7$-iso | 4-(4-methylphenoxy)-phenyl |
| 1.232 | C$_4$H$_9$-sec. | 4-(4-methylphenoxy)-phenyl |
| 1.233 | CH$_3$ | 3'-methyl-3-biphenylyl |
| 1.234 | C$_2$H$_5$ | 3'-methyl-3-biphenylyl |
| 1.235 | C$_3$H$_7$-iso | 3'-methyl-3-biphenylyl |
| 1.236 | C$_4$H$_9$-sec. | 3'-methyl-3-biphenylyl |

TABLE 1-continued

Typical representatives of compounds of formula I wherein X is
—CH(OR$_1$)— and R$_1$ is hydrogen.

| comp. no. | R$_2$ | Ph |
|---|---|---|
| 1.237 | CH$_3$ | 4-(2-methylphenoxy)-phenyl |
| 1.238 | C$_2$H$_5$ | 4-(2-methylphenoxy)-phenyl |
| 1.239 | C$_3$H$_7$-iso | 4-(2-methylphenoxy)-phenyl |
| 1.240 | C$_4$H$_9$-sec. | 4-(2-methylphenoxy)-phenyl |
| 1.241 | CH$_3$ | 3',4'-dimethyl-4-biphenylyl |
| 1.242 | C$_2$H$_5$ | 3',4'-dimethyl-4-biphenylyl |
| 1.243 | C$_3$H$_7$-iso | 3',4'-dimethyl-4-biphenylyl |
| 1.244 | C$_4$H$_9$-sec. | 3',4'-dimethyl-4-biphenylyl |
| 1.245 | CH$_3$ | 3-(2-methoxyphenoxy)-phenyl |
| 1.246 | C$_2$H$_5$ | 3-(2-methoxyphenoxy)-phenyl |
| 1.247 | C$_3$H$_7$-iso | 3-(2-methoxyphenoxy)-phenyl |
| 1.248 | C$_4$H$_9$-sec. | 3-(2-methoxyphenoxy)-phenyl |
| 1.249 | CH$_3$ | 2'-ethyl-3-biphenylyl |
| 1.250 | C$_2$H$_5$ | 2'-ethyl-3-biphenylyl |
| 1.251 | C$_3$H$_7$-iso | 2'-ethyl-3-biphenylyl |
| 1.252 | C$_4$H$_9$-sec. | 2'-ethyl-3-biphenylyl |
| 1.253 | CH$_3$ | 3'-methoxy-5'-methyl-4-biphenylyl |
| 1.254 | C$_2$H$_5$ | 3'-methoxy-5'-methyl-4-biphenylyl |
| 1.255 | C$_3$H$_7$-iso | 3'-methoxy-5'-methyl-4-biphenylyl |
| 1.256 | C$_4$H$_9$-sec. | 3'-methoxy-5'-methyl-4-biphenylyl |
| 1.257 | CH$_3$ | 4-phenoxyphenyl |
| 1.258 | C$_2$H$_5$ | 4-phenoxyphenyl |
| 1.259 | C$_3$H$_7$-iso | 4-phenoxyphenyl |
| 1.260 | C$_4$H$_9$-sec. | 4-phenoxyphenyl |
| 1.261 | CH$_3$ | 3',5'-dimethoxy-3-biphenylyl |
| 1.262 | C$_2$H$_5$ | 3',5'-dimethoxy-3-biphenylyl |
| 1.263 | C$_3$H$_7$-iso | 3',5'-dimethoxy-3-biphenylyl |
| 1.264 | C$_4$H$_9$-sec. | 3',5'-dimethoxy-3-biphenylyl |
| 1.265 | CH$_3$ | 3-(3-methylphenoxy)-phenyl |
| 1.266 | C$_2$H$_5$ | 3-(3-methylphenoxy)-phenyl |
| 1.267 | C$_3$H$_7$-iso | 3-(3-methylphenoxy)-phenyl |
| 1.268 | C$_4$H$_9$-sec. | 3-(3-methylphenoxy)-phenyl |
| 1.269 | CH$_3$ | 4-(3,4-dimethoxyphenoxy)-phenyl |
| 1.270 | C$_2$H$_5$ | 4-(3,4-dimethoxyphenoxy)-phenyl |
| 1.271 | C$_3$H$_7$-iso | 4-(3,4-dimethoxyphenoxy)-phenyl |
| 1.272 | C$_4$H$_9$-sec. | 4-(3,4-dimethoxyphenoxy)-phenyl |
| 1.273 | CH$_3$ | 4-biphenylyl |
| 1.274 | C$_2$H$_5$ | 4-biphenylyl |
| 1.275 | C$_3$H$_7$-iso | 4-biphenylyl |
| 1.276 | C$_4$H$_9$-sec. | 4-biphenylyl |
| 1.277 | CH$_3$ | 2'-methyl-3-biphenylyl |
| 1.278 | C$_2$H$_5$ | 2'-methyl-3-biphenylyl |
| 1.279 | C$_3$H$_7$-iso | 2'-methyl-3-biphenylyl |
| 1.280 | C$_4$H$_9$-sec. | 2'-methyl-3-biphenylyl |
| 1.281 | CH$_3$ | 3'-ethoxy-4-biphenylyl |
| 1.282 | C$_2$H$_5$ | 3'-ethoxy-4-biphenylyl |
| 1.283 | C$_3$H$_7$-iso | 3'-ethoxy-4-biphenylyl |
| 1.284 | C$_4$H$_9$-sec. | 3'-ethoxy-4-biphenylyl |
| 1.285 | CH$_3$ | 4-(4-methoxyphenoxy)-phenyl |
| 1.286 | C$_2$H$_5$ | 4-(4-methoxyphenoxy)-phenyl |
| 1.287 | C$_3$H$_7$-iso | 4-(4-methoxyphenoxy)-phenyl |
| 1.288 | C$_4$H$_9$-sec. | 4-(4-methoxyphenoxy)-phenyl |
| 1.289 | CH$_3$ | 3-(2-methylphenoxy)-phenyl |
| 1.290 | C$_2$H$_5$ | 3-(2-methylphenoxy)-phenyl |
| 1.291 | C$_3$H$_7$-iso | 3-(2-methylphenoxy)-phenyl |
| 1.292 | C$_4$H$_9$-sec. | 3-(2-methylphenoxy)-phenyl |
| 1.293 | CH$_3$ | 4-(3,4-dimethylphenoxy)-phenyl |
| 1.294 | C$_2$H$_5$ | 4-(3,4-dimethylphenoxy)-phenyl |
| 1.295 | C$_3$H$_7$-iso | 4-(3,4-dimethylphenoxy)-phenyl |
| 1.296 | C$_4$H$_9$-sec. | 4-(3,4-dimethylphenoxy)-phenyl |
| 1.297 | CH$_3$ | 2'-methoxy-3-biphenylyl |
| 1.298 | C$_2$H$_5$ | 2'-methoxy-3-biphenylyl |
| 1.299 | C$_3$H$_7$-iso | 2'-methoxy-3-biphenylyl |
| 1.300 | C$_4$H$_9$-sec. | 2'-methoxy-3-biphenylyl |
| 1.301 | CH$_3$ | 4'-methyl-3-biphenylyl |
| 1.302 | C$_2$H$_5$ | 4'-methyl-3-biphenylyl |
| 1.303 | C$_3$H$_7$-iso | 4'-methyl-3-biphenylyl |
| 1.304 | C$_4$H$_9$-sec. | 4'-methyl-3-biphenylyl |
| 1.305 | CH$_3$ | 4'-n-propyl-4-biphenylyl |
| 1.306 | C$_2$H$_5$ | 4'-n-propyl-4-biphenylyl |
| 1.307 | C$_3$H$_7$-iso | 4'-n-propyl-4-biphenylyl |
| 1.308 | C$_4$H$_9$-sec. | 4'-n-propyl-4-biphenylyl |
| 1.309 | CH$_3$ | 4-(3-methylphenoxy)-phenyl |
| 1.310 | C$_2$H$_5$ | 4-(3-methylphenoxy)-phenyl |
| 1.311 | C$_3$H$_7$-iso | 4-(3-methylphenoxy)-phenyl |
| 1.312 | C$_4$H$_9$-sec. | 4-(3-methylphenoxy)-phenyl |
| 1.313 | CH$_3$ | 2'-methoxy-4-biphenylyl |
| 1.314 | C$_2$H$_5$ | 2'-methoxy-4-biphenylyl |
| 1.315 | C$_3$H$_7$-iso | 2'-methoxy-4-biphenylyl |
| 1.316 | C$_4$H$_9$-sec. | 2'-methoxy-4-biphenylyl |
| 1.317 | CH$_3$ | 4'-n-propoxy-4-biphenylyl |
| 1.318 | C$_2$H$_5$ | 4'-n-propoxy-4-biphenylyl |
| 1.319 | C$_3$H$_7$-iso | 4'-n-propoxy-4-biphenylyl |
| 1.320 | C$_4$H$_9$-sec. | 4'-n-propoxy-4-biphenylyl |
| 1.321 | CH$_3$ | 3',4'-dimethyl-3-biphenylyl |
| 1.322 | C$_2$H$_5$ | 3',4'-dimethyl-3-biphenylyl |
| 1.323 | C$_3$H$_7$-iso | 3',4'-dimethyl-3-biphenylyl |
| 1.324 | C$_4$H$_9$-sec. | 3',4'-dimethyl-3-biphenylyl |
| 1.325 | CH$_3$ | 3'-methyl-4'-methoxy-4-biphenylyl |
| 1.326 | C$_2$H$_5$ | 3'-methyl-4'-methoxy-4-biphenylyl |
| 1.327 | C$_3$H$_7$-iso | 3'-methyl-4'-methoxy-4-biphenylyl |
| 1.328 | C$_4$H$_9$-sec. | 3'-methyl-4'-methoxy-4-biphenylyl |
| 1.329 | CH$_3$ | 3-(4-methylphenoxy)-phenyl |
| 1.330 | C$_2$H$_5$ | 3-(4-methylphenoxy)-phenyl |
| 1.331 | C$_3$H$_7$-iso | 3-(4-methylphenoxy)-phenyl |
| 1.332 | C$_4$H$_9$-sec. | 3-(4-methylphenoxy)-phenyl |
| 1.333 | CH$_3$ | 3',4',5'-trimethyl-3-biphenylyl |
| 1.334 | C$_2$H$_5$ | 3',4',5'-trimethyl-3-biphenylyl |
| 1.335 | C$_3$H$_7$-iso | 3',4',5'-trimethyl-3-biphenylyl |
| 1.336 | C$_4$H$_9$-sec. | 3',4',5'-trimethyl-3-biphenylyl |
| 1.337 | CH$_3$ | 2'-ethoxy-4-biphenylyl |
| 1.338 | C$_2$H$_5$ | 2'-ethoxy-4-biphenylyl |
| 1.339 | C$_3$H$_7$-iso | 2'-ethoxy-4-biphenylyl |
| 1.340 | C$_4$H$_9$-sec. | 2'-ethoxy-4-biphenylyl |
| 1.341 | CH$_3$ | 4'-methyl-4-biphenylyl |
| 1.342 | C$_2$H$_5$ | 4'-methyl-4-biphenylyl |
| 1.343 | C$_3$H$_7$-iso | 4'-methyl-4-biphenylyl |
| 1.344 | C$_4$H$_9$-sec. | 4'-methyl-4-biphenylyl |
| 1.345 | CH$_3$ | 3',4'-dimethoxy-3-biphenylyl |
| 1.346 | C$_2$H$_5$ | 3',4'-dimethoxy-3-biphenylyl |
| 1.347 | C$_3$H$_7$-iso | 3',4'-dimethoxy-3-biphenylyl |
| 1.348 | C$_4$H$_9$-sec. | 3',4'-dimethoxy-3-biphenylyl |
| 1.349 | CH$_3$ | 3-(3,5-dimethoxyphenoxy)-phenyl |
| 1.350 | C$_2$H$_5$ | 3-(3,5-dimethoxyphenoxy)-phenyl |
| 1.351 | C$_3$H$_7$-iso | 3-(3,5-dimethoxyphenoxy)-phenyl |
| 1.352 | C$_4$H$_9$-sec. | 3-(3,5-dimethoxyphenoxy)-phenyl |
| 1.353 | CH$_3$ | 3',4'-dimethoxy-4-biphenylyl |
| 1.354 | C$_2$H$_5$ | 3',4'-dimethoxy-4-biphenylyl |
| 1.355 | C$_3$H$_7$-iso | 3',4'-dimethoxy-4-biphenylyl |
| 1.356 | C$_4$H$_9$-sec. | 3',4'-dimethoxy-4-biphenylyl |
| 1.357 | CH$_3$ | 4'-ethoxy-3-biphenylyl |
| 1.358 | C$_2$H$_5$ | 4'-ethoxy-3-biphenylyl |
| 1.359 | C$_3$H$_7$-iso | 4'-ethoxy-3-biphenylyl |
| 1.360 | C$_4$H$_9$-sec. | 4'-ethoxy-3-biphenylyl |
| 1.361 | CH$_3$ | 3'-methyl-4-biphenylyl |
| 1.362 | C$_2$H$_5$ | 3'-methyl-4-biphenylyl |
| 1.363 | C$_3$H$_7$-iso | 3'-methyl-4-biphenylyl |
| 1.364 | C$_4$H$_9$-sec. | 3'-methyl-4-biphenylyl |
| 1.365 | CH$_3$ | 3'-methoxy-3-biphenylyl |
| 1.366 | C$_2$H$_5$ | 3'-methoxy-3-biphenylyl |
| 1.367 | C$_3$H$_7$-iso | 3'-methoxy-3-biphenylyl |
| 1.368 | C$_4$H$_9$-sec. | 3'-methoxy-3-biphenylyl |
| 1.369 | CH$_3$ | 3',5'-dimethyl-4-biphenyl |
| 1.370 | C$_2$H$_5$ | 3',5'-dimethyl-4-biphenyl |
| 1.371 | C$_3$H$_7$-iso | 3',5'-dimethyl-4-biphenyl |
| 1.372 | C$_4$H$_9$-sec. | 3',5'-dimethyl-4-biphenyl |
| 1.373 | CH$_3$ | 4'-methoxy-4-biphenylyl |
| 1.374 | C$_2$H$_5$ | 4'-methoxy-4-biphenylyl |
| 1.375 | C$_3$H$_7$-iso | 4'-methoxy-4-biphenylyl |
| 1.376 | C$_4$H$_9$-sec. | 4'-methoxy-4-biphenylyl |
| 1.377 | CH$_3$ | 3'-methoxy-4-biphenylyl |
| 1.378 | C$_2$H$_5$ | 3'-methoxy-4-biphenylyl |
| 1.379 | C$_3$H$_7$-iso | 3'-methoxy-4-biphenylyl |
| 1.380 | C$_4$H$_9$-sec. | 3'-methoxy-4-biphenylyl |
| 1.381 | CH$_3$ | 5-methyl-3-biphenylyl |
| 1.382 | C$_2$H$_5$ | 5-methyl-3-biphenylyl |
| 1.383 | C$_3$H$_7$-iso | 5-methyl-3-biphenylyl |
| 1.384 | C$_4$H$_9$-sec. | 5-methyl-3-biphenylyl |
| 1.385 | CH$_3$ | 2-methoxy-4-(3-methylphenoxy)-phenyl |
| 1.386 | C$_2$H$_5$ | 2-methoxy-4-(3-methylphenoxy)-phenyl |
| 1.387 | C$_3$H$_7$-iso | 2-methoxy-4-(3-methylphenoxy)-phenyl |
| 1.388 | C$_4$H$_9$-sec. | 2-methoxy-4-(3-methylphenoxy)-phenyl |
| 1.389 | CH$_3$ | 4'-methoxy-2-methyl-4-biphenylyl |
| 1.390 | C$_2$H$_5$ | 4'-methoxy-2-methyl-4-biphenylyl |

TABLE 1-continued

Typical representatives of compounds of formula I wherein X is —CH(OR₁)— and R₁ is hydrogen.

| comp. no. | R₂ | Ph |
|---|---|---|
| 1.391 | C₃H₇-iso | 4'-methoxy-2-methyl-4-biphenylyl |
| 1.392 | C₄H₉-sec. | 4'-methoxy-2-methyl-4-biphenylyl |
| 1.393 | CH₃ | 5-methoxy-3-biphenylyl |
| 1.394 | C₂H₅ | 5-methoxy-3-biphenylyl |
| 1.395 | C₃H₇-iso | 5-methoxy-3-biphenylyl |
| 1.396 | C₄H₉-sec. | 5-methoxy-3-biphenylyl |

TABLE 2

Typical representatives of compounds of formula I wherein X is —C(O)—.

| comp. no. | R₂ | Ph |
|---|---|---|
| 2.1 | CH₃ | 4-biphenylyl |
| 2.2 | C₂H₅ | 4-biphenylyl |
| 2.3 | C₃H₇-iso | 4-biphenylyl |
| 2.4 | C₄H₉-sec. | 4-biphenylyl |
| 2.5 | CH₃ | 3-methylphenyl |
| 2.6 | C₂H₅ | 3-methylphenyl |
| 2.7 | C₃H₇-iso | 3-methylphenyl |
| 2.8 | C₄H₉-sec. | 3-methylphenyl |
| 2.9 | CH₃ | 3-biphenylyl |
| 2.10 | C₂H₅ | 3-biphenylyl |
| 2.11 | C₃H₇-iso | 3-biphenylyl |
| 2.12 | C₄H₉-sec. | 3-biphenylyl |
| 2.13 | CH₃ | phenyl |
| 2.14 | C₂H₅ | phenyl |
| 2.15 | C₃H₇-iso | phenyl |
| 2.16 | C₄H₉-sec. | phenyl |
| 2.17 | CH₃ | 2-methylphenyl |
| 2.18 | C₂H₅ | 2-methylphenyl |
| 2.19 | C₃H₇-iso | 2-methylphenyl |
| 2.20 | C₄H₉-sec. | 2-methylphenyl |
| 2.21 | CH₃ | 4-methoxyphenyl |
| 2.22 | C₂H₅ | 4-methoxyphenyl |
| 2.23 | C₃H₇-iso | 4-methoxyphenyl |
| 2.24 | C₄H₉-sec. | 4-methoxyphenyl |
| 2.25 | CH₃ | 3-methoxyphenyl |
| 2.26 | C₂H₅ | 3-methoxyphenyl |
| 2.27 | C₃H₇-iso | 3-methoxyphenyl |
| 2.28 | C₄H₉-sec. | 3-methoxyphenyl |
| 2.29 | CH₃ | 2-methoxyphenyl |
| 2.30 | C₂H₅ | 2-methoxyphenyl |
| 2.31 | C₃H₇ | 2-methoxyphenyl |
| 2.32 | C₄H₉-sec. | 2-methoxyphenyl |
| 2.33 | CH₃ | 3,4-dimethoxyphenyl |
| 2.34 | C₂H₅ | 3,4-dimethoxyphenyl |
| 2.35 | C₃H₇-iso | 3,4-dimethoxyphenyl |
| 2.36 | C₄H₉-sec. | 3,4-dimethoxyphenyl |
| 2.37 | CH₃ | 4-phenoxyphenyl |
| 2.38 | C₂H₅ | 4-phenoxyphenyl |
| 2.39 | C₃H₇-iso | 4-phenoxyphenyl |
| 2.40 | C₄H₉-sec. | 4-phenoxyphenyl |
| 2.41 | CH₃ | 4-methylphenyl |
| 2.42 | C₂H₅ | 4-methylphenyl |
| 2.43 | C₃H₇-iso | 4-methylphenyl |
| 2.44 | C₄H₉-sec. | 4-methylphenyl |

TABLE 3

Typical representatives of compounds of formula I wherein X is —C(=N—OR)— and R is hydrogen.

| comp. no. | R₂ | Ph |
|---|---|---|
| 3.1 | CH₃ | 4-biphenylyl |
| 3.2 | C₂H₅ | 4-biphenylyl |
| 3.3 | C₃H₇-iso | 4-biphenylyl |
| 3.4 | C₄H₉-sek | 4-biphenylyl |
| 3.5 | CH₃ | 3-methylphenyl |
| 3.6 | C₂H₅ | 3-methylphenyl |
| 3.7 | C₃H₇-iso | 3-methylphenyl |
| 3.8 | C₄H₉-sek | 3-methylphenyl |
| 3.9 | CH₃ | 3-biphenyl |
| 3.10 | C₂H₅ | 3-biphenyl |
| 3.11 | C₃H₇-iso | 3-biphenyl |
| 3.12 | C₄H₉-sek | 3-biphenyl |
| 3.13 | CH₃ | phenyl |
| 3.14 | C₂H₅ | phenyl |
| 3.15 | C₃H₇-iso | phenyl |
| 3.16 | C₄H₉-sek | phenyl |
| 3.17 | CH₃ | 2-methylphenyl |
| 3.18 | C₂H₅ | 2-methylphenyl |
| 3.19 | C₃H₇-iso | 2-methylphenyl |
| 3.20 | C₄H₉-sek | 2-methylphenyl |
| 3.21 | CH₃ | 4-methoxyphenyl |
| 3.22 | C₂H₅ | 4-methoxyphenyl |
| 3.23 | C₃H₇-iso | 4-methoxyphenyl |
| 3.24 | C₄H₉-sek | 4-methoxyphenyl |
| 3.25 | CH₃ | 3-methoxyphenyl |
| 3.26 | C₂H₅ | 3-methoxyphenyl |
| 3.27 | C₃H₇-iso | 3-methoxyphenyl |
| 3.28 | C₄H₉-sek | 3-methoxyphenyl |
| 3.29 | CH₃ | 2-methoxyphenyl |
| 3.30 | C₂H₅ | 2-methoxyphenyl |
| 3.31 | C₃H₇ | 2-methoxyphenyl |
| 3.32 | C₄H₉-sek | 2-methoxyphenyl |
| 3.33 | CH₃ | 3,4-dimethoxyphenyl |
| 3.34 | C₂H₅ | 3,4-dimethoxyphenyl |
| 3.35 | C₃H₇-iso | 3,4-dimethoxyphenyl |
| 3.36 | C₄H₉-sek | 3,4-dimethoxyphenyl |
| 3.37 | CH₃ | 4-phenoxyphenyl |
| 3.38 | C₂H₅ | 4-phenoxyphenyl |
| 3.39 | C₃H₇-iso | 4-phenoxyphenyl |
| 3.40 | C₄H₉-sek | 4-phenoxyphenyl |
| 3.41 | CH₃ | 4-methylphenyl |
| 3.42 | C₂H₅ | 4-methylphenyl |
| 3.43 | C₃H₇-iso | 4-methylphenyl |
| 3.44 | C₄H₉-sek | 4-methylphenyl |

Formulation Examples for the compound of formula I (throughout, percentages are by weight)

| Wettable powders | a) | b) | c) |
|---|---|---|---|
| a compound of Examples P1–P12 | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is throughly mixed with the adjuvants and the mixture is thoroughly ground in a suitable mill, affording wettable powders which can be diluted with water to give suspensions of the desired concentration.

| Emulsifiable concentrate | |
|---|---|
| a compound of Examples P1–P12 | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | a) | b) |
|---|---|---|
| a compound of Examples P1–P12 | 5% | 8% |
| talcum | 95% | — |
| kaolin | — | 92% |

Ready-for-use dusts are obtained by mixing the active ingredient with the carrier and grinding the mixture in a suitable mill.

| Extruder granulate | |
|---|---|
| a compound of Examples P1–P12 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Tablets or boli | | |
|---|---|---|
| I | a compound of Examples P1–P12 | 33.0% |
| | methylcellulose | 0.80% |
| | highly dispersed silicic acid | 0.80% |
| | maize starch | 8.40% |

The methyl cellulose is stirred into water and allowed to swell, and the silicic acid is stirred in to give a homogeneous suspension. The active ingredient and the maize starch are mixed, and the aqueous suspension is incorporated into the mixture, which is then kneaded to a paste. This mass is granulated through a sieve (mesh width 12M) and then dried.

| II | lactose cryst. | 22.50% |
|---|---|---|
| | maize starch | 17.00% |
| | microcrystalline cellulose | 16.50% |
| | magnesium stearate | 1.00% |

All four adjuvants are thoroughly mixed.

Phases I and II are mixed and compressed to form tablets or boli.

| Injectable composition | |
|---|---|
| A. Oily vehicle (slow release) | |
| a compound of Examples P1–P12 | 0.1–1.0 g |
| groundnut oil | ad 100 ml |
| a compound of Examples P1–P12 | 0.1–1.0 g |
| sesame oil | ad 100 ml |

Preparation: The active ingredient is dissolved in a portion of the oil while stirring and, if necessary, while heating gently. After cooling, the solution is made up to the prescribed volume and sterile-filtered through a suitable membrane filter having a pore diameter of 0.22 μm.

| B. Water-miscible solvent (medium release rate) | |
|---|---|
| a compound of Examples P1–P12 | 0.1–1.0 g |
| 4-hydroxymethyl-1,3-dioxolane (glycerol formal) | 40 g |
| 1,2-propanediol | ad 100 ml |
| a compound of Examples P1–P12 | 0.1–1.0 g |
| glycerin dimethyl ketal | 40 g |

-continued

| B. Water-miscible solvent (medium release rate) | |
|---|---|
| 1,2-propanediol | ad 100 ml |

Preparation: The active ingredient is dissolved in a portion of the solvent while stirring, and the solution is made up to the prescribed volume and sterile-filtered through a suitable membrane filter having a pore diameter of 0.22 μm.

| C. Aqueous solubilisate (rapid release) | |
|---|---|
| a compound of Examples P1–P12 | 0.1–1.0 g |
| polyethoxylated castor oil (40 ethylene oxide units)* | 10 g |
| 1,2-propanediol | 20 g |
| benzyl alcohol | 1 g |
| aqua ad inject. | ad 100 ml |
| a compound of Examples P1–P12 | 0.1–1.0 g |
| polyethoxylated sorbitan monooleate (20 ethylene oxide units)** | 8 g |
| 4-hydroxymethyl-1,3-dioxolane (glycerol formal) | 20 g |
| benzyl alcohol | 1 g |
| aqua ad inject. | ad 100 ml |

*Obtainable commercially under the name CREMOPHOR ® EL (BASF AG);
**Obtainable commercially under the name TWEEN ® 80 (ICI);

Preparation: The active ingredient is dissolved in the solvents and the surfactant, and the solution is made up to the prescribed volume with water and then sterile-filtered through a suitable membrane filter of 0.22 μm pore diameter.

The aqueous systems may preferably be used also for oral and/or intraruminal administration.

BIOLOGICAL EXAMPLES

B-1. Action against $L_1$-larvae of *Lucilia sericata*

1 ml of an aqueous suspension of the test compound is mixed in such a manner with 3 ml of a special larval culture medium at about 50° C. that a homogeneous composition containing, as desired, 250 ppm or 125 ppm of active ingredient is obtained. About 30 Lucilia larvae ($L_1$) are put into each of a number of test tubes containing the test composition. The mortality rate is determined after 4 days. Compounds of formula I, for example those of Examples P1 to P12, achieve complete kill at 250 ppm.

B-2. Acaricidal Action against *Boophilus microplus* (Biarra Strain)

Adhesive tape is applied horizontally across a PVC plate in such a manner that 10 female *Boophilus microplus* ticks (Biarra strain) fully replete with blood can be affixed thereto in the dorsal position side by side in a row. Using an injection needle, each tick is injected with 1 μl of a liquid consisting of a 1:1 mixture of polyethylene glycol and acetone in which a specific amount of active ingredient of 1.0 μg per tick has been dissolved. Control ticks receive an injection that does not contain active ingredient. After treatment, the ticks are kept in an insectarium under normal conditions at about 28° C. and 80% relative humidity until oviposition has taken place and the larvae have hatched from the eggs of the control ticks.

The activity of a tested compound is determined by the $IR_{90}$, i.e. that dose of active ingredient is determined at which 9 out of 10 female ticks (90%), even after 30 days, lay eggs from which larvae are unable to hatch.

Compounds of formula I, for example of Examples P1–P12, exhibit an IR90 at a dosage of 5 μg/g.

B-3. Trial with Sheep Infested with Nematodes (*Haemonchus contortus* and *Trichostrongylus colubriformis*)

The active ingredient is formulated as a suspension and administered using a stomach probe or by intraruminal injection to sheep that have been artificially infested with *Haemonchus contortus* and *Trichostrongylus colubriformis*. 1 to 3 animals are used for each dose. Each sheep is treated once only with a single dose of, as desired, 1 mg or 0.5 mg/kg of body weight. Evaluation is made by comparing the number of worm eggs excreted in the faeces of the sheep before and after treatment.

Sheep infested simultaneously and in the same manner but untreated are used as controls. In comparison with untreated but infested control groups, sheep that have been treated with compounds of formula I, for example those of Examples P1 to P12 at 1 mg/kg, show no nematode infestation (=complete reduction of the worm eggs in the faeces).

B-4. Larvicidal Action against *Äedes aegypti*

A 0.1% solution of the active ingredient in acetone is pipetted onto the surface of 150 ml of water in each of a number of containers in amounts sufficient to give concentrations of, as desired, 10 ppm, 3.3 ppm and 1.6 ppm. After the acetone has evaporated, about 30 to 40 3-day-old Äedes larvae are put into each container. Mortality counts are made after 1, 2 and 5 days.

In this test, compounds of formula I, such as, for example, those of Examples P1 to P12, achieve complete kill of all larvae at low concentration after only one day.

B-5. Miticidal Action against *Dermanyssus gallinae*

2 to 3 ml of a test solution containing 100 ppm of active ingredient are put into a glass container which is open at the top, and about 200 mites in different stages of development are put into this container. The glass container is sealed with a wad of cotton wool and is uniformly shaken for 10 minutes until the mites have been completely wetted. The container is then inverted until excess test solution has been absorbed by the cotton wool. The container is then stood upright again and the treated mites are kept under observation for three days under laboratory conditions in order to evaluate the effectiveness of the test compounds. Mortality is the criterion for effectiveness.

Compounds of Preparation Examples P1 to P12 achieve a kill of the mites at the stated concentration.

What is claimed is:

1. A process for the preparation of compounds of formula I

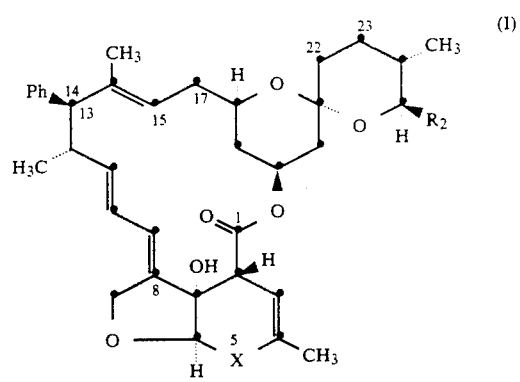

in which

X is one of the groups —CH(OR$_1$)—, or —C(=O)—or —C(=N—OR)—;

R$_1$ is hydrogen, or an OH-protecting group;

R is hydrogen, an OH-protecting group, an alkyl group or a cycloakyl group;

R$_2$ methyl, ethyl, isopropyl or sec.-butyl; and

Ph is a phenyl ring that is substituted by R$_a$, R$_b$, R$_c$ and R$_d$, wherein each of R$_a$, R$_b$, R$_c$ and R$_d$, independently of the others, is hydrogen, C$_1$–C$_{10}$alkyl, C$_2$–C$_{10}$alkoxyalkyl, C$_2$–C$_{10}$alkenyl, C$_1$–C$_{10}$alkoxy, C$_2$–C$_{10}$alkoxyalkoxy, or a phenyl or phenoxy radical that is unsubstituted or is substituted by at least one substituent from the group C$_1$–C$_3$alkyl and C$_1$–C$_3$alkoxy;

which process comprises the step of reacting a compound of formula II

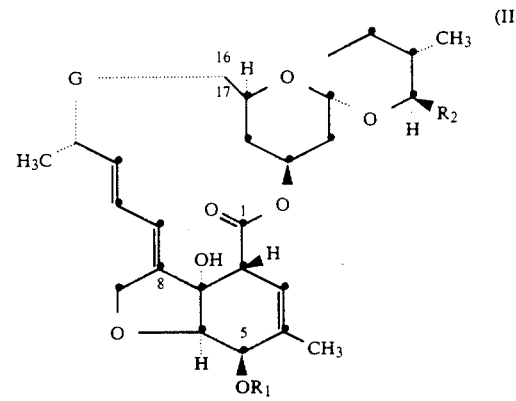

wherein G is one of the groups a or b

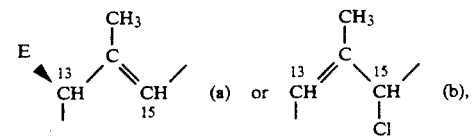

[= 13β-halogen-Δ$^{14,15}$]   [= 15-chloro-Δ$^{13,14}$]

and E is chlorine, bromine or iodine;

with a diaryl zinc compound of formula III

Ph—Zn—Ph   (III), in the presence of a transition metal salt selected from the group consisting of phosphines and amines of Fe, Ru, Os, Co, Rh, Ir, Ni, Pd and Pt substituted by organic residues, and, if desired, when $R_1$ is an OH-protecting group, removing that protecting group by hydrolysis, and in order to obtain compounds of formula I wherein X is C=O, treating compounds of formula I wherein X is —CH(OH)—with a reagent suitable for the purpose of oxidation or with a ketone in the presence of an aluminium alcoholate; and in order to obtain compounds of formula I wherein X is C(=NOR), reacting compounds of formula I wherein X is C=O with hydroxylamine or a salt thereof and, if desired, subsequently introducing the substituent R, or carrying out the reaction with a compound of formula $NH_2$—OR or with a salt thereof wherein R in each case has the meanings given for formula I with the exception of hydrogen.

2. A process according to claim 1, which comprises carrying out the reaction in the presence of a transition metal salt that contains, as the metal component, Co, Ni or Pd.

3. A process according to claim 1, which comprises using as the transition metal salt $NiCl_2$, $CoCl_2$, [(phenyl)$_3$P]$_2$NiCl$_2$, [(phenyl)$_3$P]$_2$PdCl$_2$, [(phenyl)$_2$PCH$_2$]$_2$NiCl$_2$, [(phenyl)$_2$PCH$_2$CoBr$_2$, [(phenyl)$_2$PCH$_2$CH$_2$CH$_2$P-(phenyl)$_2$]NiCl$_2$, [(phenyl)$_2$PCH$_2$CH$_2$]$_2$NiCl$_2$ or [(cyclohexyl)$_3$P]$_2$NiCl$_2$.

* * * * *